United States Patent [19]

Iwahara et al.

[11] Patent Number: 5,567,833
[45] Date of Patent: Oct. 22, 1996

[54] CURING AGENT, PREPARATION THEREOF AND CURABLE COMPOSITION COMPRISING THE SAME

[75] Inventors: Takahisa Iwahara; Makoto Chiba; Tomoko Takahara; Kazuya Yonezawa, all of Kobe, Japan

[73] Assignee: Kanegafuchi Chemical Industry Co., Ltd., Osaka, Japan

[21] Appl. No.: 313,923

[22] Filed: Sep. 26, 1994

Related U.S. Application Data

[62] Division of Ser. No. 29,993, Mar. 8, 1993, Pat. No. 5,409,995, which is a continuation of Ser. No. 640,415, Jan. 28, 1991, abandoned.

[30] Foreign Application Priority Data

| May 29, 1989 | [JP] | Japan | 1-135666 |
| May 29, 1989 | [JP] | Japan | 1-135667 |
| May 29, 1989 | [JP] | Japan | 1-135668 |
| Jun. 1, 1989 | [JP] | Japan | 1-139940 |
| Jun. 7, 1989 | [JP] | Japan | 1-145672 |
| Jun. 7, 1989 | [JP] | Japan | 1-145673 |
| Jun. 7, 1989 | [JP] | Japan | 1-145674 |
| Jun. 15, 1989 | [JP] | Japan | 1-153143 |
| May 29, 1990 | [WO] | WIPO | PCT/SP90/00686 |

[51] Int. Cl.[6] .................................. C07F 7/08
[52] U.S. Cl. ................. 556/434; 556/437; 556/440; 556/445; 556/451
[58] Field of Search ............... 556/451, 434, 556/437, 440, 445

[56] References Cited

U.S. PATENT DOCUMENTS

| 4,895,967 | 1/1990 | Crivello et al. | 556/451 |
| 5,189,193 | 2/1993 | Freeburne et al. | 556/451 |
| 5,194,649 | 3/1993 | Okawa | 556/451 |
| 5,241,097 | 8/1993 | Zupancic et al. | 556/451 |
| 5,256,754 | 10/1993 | Takarada et al. | 556/451 X |
| 5,272,243 | 12/1993 | Nakashima et al. | 556/451 |

FOREIGN PATENT DOCUMENTS

| 255440 | 2/1988 | European Pat. Off. . |
| 259711 | 3/1988 | European Pat. Off. . |
| 1071952 | 8/1958 | Germany . |
| 48-93658 | 12/1973 | Japan . |
| 52-85123 | 7/1977 | Japan . |
| 381239 | 2/1983 | Japan . |
| 58-217505 | 12/1983 | Japan . |
| 60-120755 | 6/1985 | Japan . |
| 62-49305 | 3/1987 | Japan . |
| 6422967 | 1/1989 | Japan . |

*Primary Examiner*—Paul F. Shaver
*Attorney, Agent, or Firm*—Foley & Lardner

[57] ABSTRACT

A curable composition which comprises (C) a non-polymeric organic curing agent having at least two hydrosilyl groups in a molecule, (D) an organic polymer having at least one alkenyl group in a molecule, and (E) a hydrosilylation catalyst has rapid curability and good depth curability, and gives a homogeneous cured material having good mechanical properties.

5 Claims, 3 Drawing Sheets

CURING AGENT, PREPARATION THEREOF AND CURABLE COMPOSITION COMPRISING THE SAME

This application is a division of Ser. No. 08/029,993 filed Mar. 8, 1993, now U.S. Pat. No. 5,409,995, which is a continuation of Ser. No. 07/640,415, filed Jan. 28, 1991, now abandoned.

FIELD OF THE INVENTION

The present invention relates to an organic curable agent having a hydrosilyl group, a preparation thereof, and a curable composition comprising said curing agent.

BACKGROUND ART

Hitherto, various curable liquid compositions which are cured to give rubbery materials have been developed. Among them, a curing system having good depth curability has been developed, which system is prepared by cross-linking a polyorganosiloxane having on the average two or more vinyl groups at a molecular end or in a molecular chain of one molecule with a polyorganohydrogensiloxane having two or more hydrogen atoms bonded to silicon atoms in one molecule. Such system is used as a sealing agent or a potting agent by utilizing its good weather resistance, water resistance and thermal resistance. However, such system has limited applications because a cost is high, an adhesion property is not good and fungus easily grows. Further, said polyorganosiloxane generally has poor compatibility with an organic polymer. When a polyorganohydrogensiloxane and an organic polymer having an alkenyl group are intended to be cured, hydrolysis and a dehydrogenation condensation reaction of the polyorganohydrogensiloxane are promoted owing to phase separation, and thus sufficient mechanical properties are not achieved because of voids.

SUMMARY OF THE INVENTION

As the result of an extensive study under such circumstances, the present invention solves these problems and provides a curable liquid composition having rapid curability and good depth curability, an organic curing agent having hydrosilyl groups in a molecule which is suitable to give such composition, and a preparation of the curing agent.

When a non-polymeric organic curing agent which has at least two hydrosilyl groups in a molecule is used instead of a polyorganohydrogensiloxane conventionally used for a curing reaction through a hydrosilylation, it has good compatibility with an organic polymer having alkenyl groups. We discovered that, a curable composition which is homogeneous, has rapid curability and good depth curability and gives a cured material having sufficient mechanical properties such as tensile properties is obtained, when said two components are mixed with a hydrosilylation catalyst and then cured; that since an alkenyl group-containing organic polymer having any kind of backbones can be used, it is possible to prepare a cured material which can be used for very various applications; and that since an organic curing agent which is not a polymer generally has a low viscosity, an operation can be advantageously carried out during a preparation of a cured material. Then, we completed the present invention.

The first aspect of the present invention resides in a non-polymeric organic curing agent having at least two hydrosilyl groups in a molecule.

The second aspect of the present invention resides in a method for preparing a non-polymeric organic curing agent having an least two hydrosilyl groups in a molecule, which method comprises reacting (A) an organic compound having at least one alkenyl group in a molecule with (B) a polyvalent hydrogensilicon compound in the presence of a hydrosilylation catalyst so that the hydrosilyl groups remain after the reaction.

The third aspect of the present invention resides in a curable composition which comprises (C) a non-polymeric organic curing agent having at least two hydrosilyl groups in a molecule, (D) an organic polymer having at least one alkenyl group in a molecule, and (E) a hydrosilylation catalyst.

DETAILED DESCRIPTION OF THE INVENTION

Figure 1:
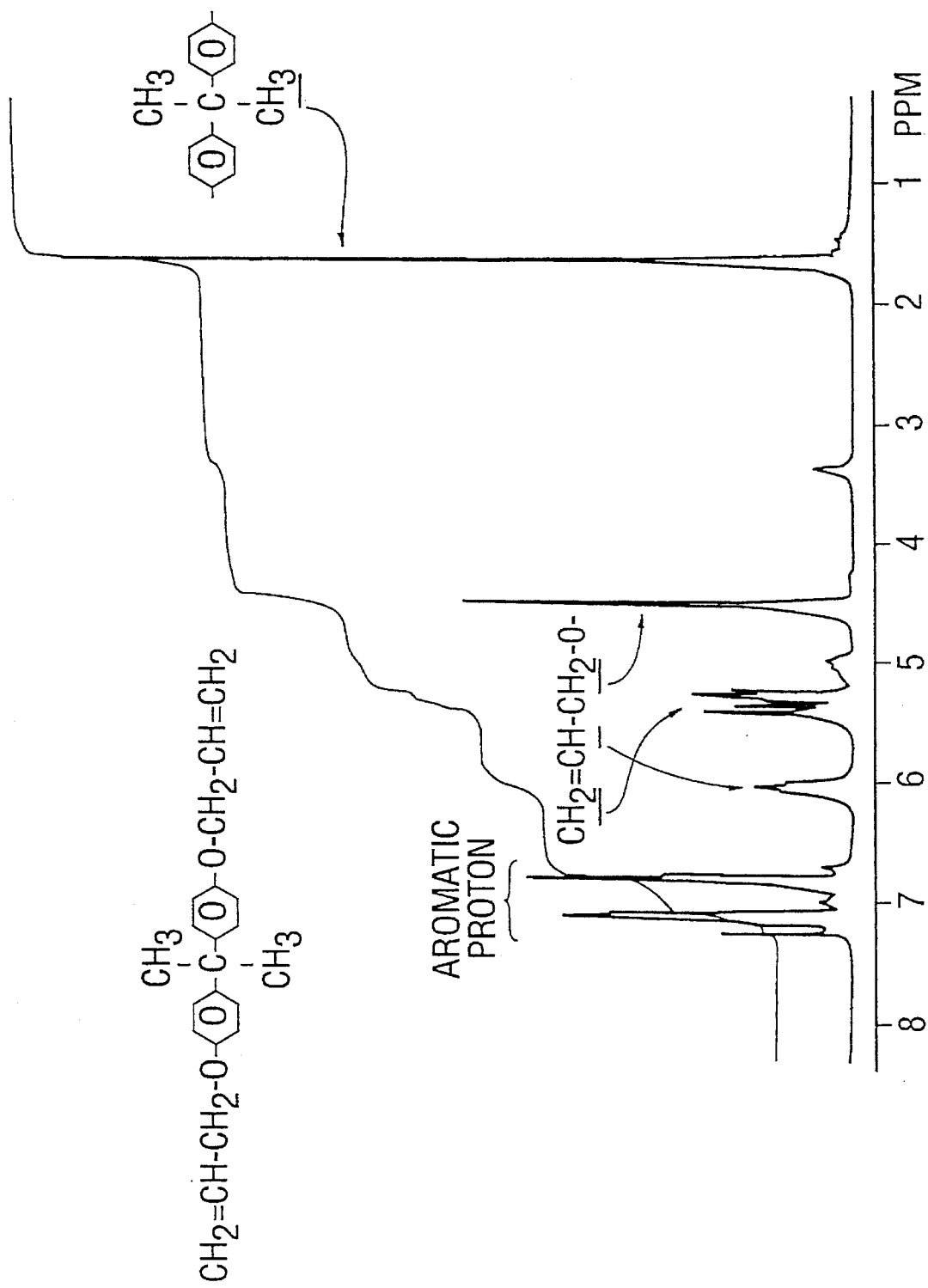
FIG. 1 is a 300 MHz $^1$H NMR spectrum chart of the diallyl ether of bisphenol A obtained in Preparative Example 1.

The organic compound having at least two hydrosilyl groups in a molecule which is not a polymer according to the first aspect of the present invention is not limited. Specific examples of a group having the hydrosilyl group are a hydrosilyl-containing group having only one silicon atom such as —Si(H)$_n$(CH$_3$)$_{3-n}$, —Si(H)$_n$(C$_2$H$_5$)$_{3-n}$, —Si(H)$_n$(C$_6$H$_5$)$_{3-n}$ (n=1 to 3), —SiH$_2$(C$_6$H$_{13}$);
a group having at least two silicon atoms such as —Si(CH$_3$)$_2$Si(CH$_3$)$_2$H, —Si(CH$_3$)$_2$CH$_2$CH$_2$Si(CH$_3$)$_2$H, —Si(CH$_3$)$_2$Si(CH$_3$)H$_2$,

—Si(CH$_3$)$_2$NHSi(CH$_3$)$_2$H, —Si(CH$_3$)$_2$N[Si(CH$_3$)$_2$H]$_2$,

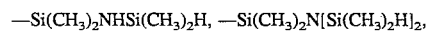

a group derived from various linear, branched and cyclic polyvalent hydrogensiloxanes of the formulas:

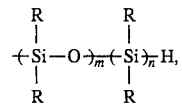

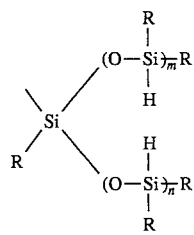

(wherein each R is, same or different, a group selected from H, OSi(CH$_3$)$_3$ or an organic group having 1 to 10 carbon atoms, and m and n are positive integers provided that $2 \leq m+n \leq 50$.)

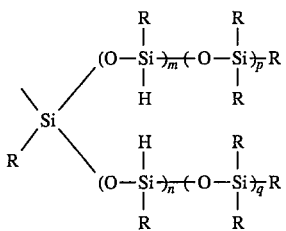

(wherein R is the same as the above, and m is a positive integer and n, p and q are 0 or positive integers provided that $1 \leq m+n+p+q \leq 50$.) and

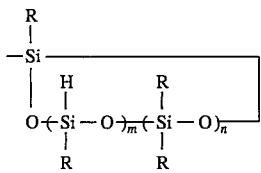

(wherein R is the same as the above, and m is a positive integer and n is 0 or a positive integer provided that $2 \leq m+n \leq 50$.).

Among the above various hydrosilyl-containing groups, a group having the hydrosilyl group preferably has a molecular weight of lower than 500, since the organic curing agent having the hydrosilyl groups according to the present invention has a low possibility to decrease the compatibility with various organic polymers. The following groups are preferable further in view of reactivity of the hydrosilyl group:

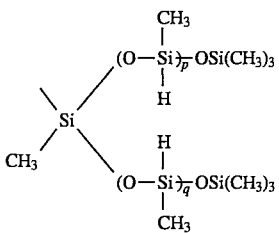

(wherein p is a positive integer and q is 0 or a positive integer provided that $2 \leq p+q \leq 4$.),

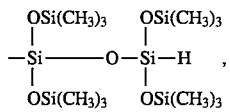

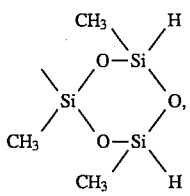

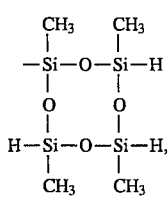

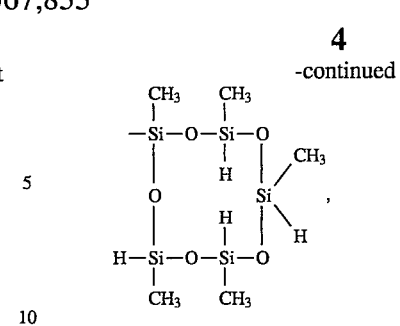

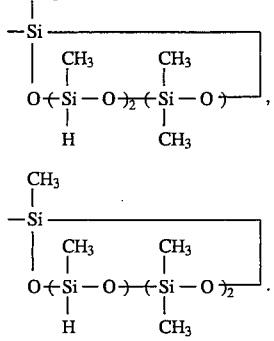

When at least two hydrosilyl-containing groups are present in one molecule, these may be same or different.

The total number of hydrosilyl groups in one molecule of the organic curing agent having the hydrosilyl group which is not a polymer is at least 2, preferably 2 to 15, particularly 3 to 12. In case that the hydrosilyl group-containing organic curing agent according to the present invention is mixed with various alkenyl group-containing organic polymers in the presence of the hydrosilylation catalyst so as to give a cured material through a hydrosilylation reaction, the curing tends to be slow and insufficient if the number of the hydrosilyl groups is smaller than 2. When the number of the hydrosilyl groups is larger than 15, the curing agent has bad stability and the cured material has still a large number of the hydrosilyl groups after the curing which cause voids and cracking.

The hydrosilyl group in the hydrosilyl group-containing organic curing agent according to the present invention is preferably a group of the formula:

$$X-R^2- \qquad (II)$$

wherein X is a substituting group having at least one hydrosilyl group, and $R^2$ is a divalent hydrocarbon group having 2 to 20 carbon atoms which may have at least one ether linkage. One example of the curing agent is a compound having an ether linkage of the formula:

$$(X-R^2-O)_a R^3 \qquad (III)$$

wherein X and $R^2$ are the same as the above, $R^3$ is an organic group having 1 to 30 carbon atoms and a is an integer of 1 to 4.

In the formula (III), $R^2$ represents a divalent hydrocarbon group having 2 to 20 carbon atoms, and may include at least one ether linkage. Specific examples of $R^2$ are $-CH_2CH_2-$, $-CH_2CH_2CH_2-$,

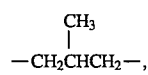

$-CH_2CH_2CH_2CH_2-$, $-CH_2CH_2O-CH_2CH_2-$ and $-CH_2CH_2O-CH_2CH_2CH_2-$. $-CH_2CH_2CH_2-$ is preferable because of the easiness of its preparation.
In the formula (III), $R^3$ is a mono-, di-, tri- or tetra-valent organic aromatic or aliphatic group having 1 to 30 carbon atoms. Specific examples of $R^3$ are $CH_3-$, $CH_3CH_2-$, $CH_3CH_2CH_2-$,
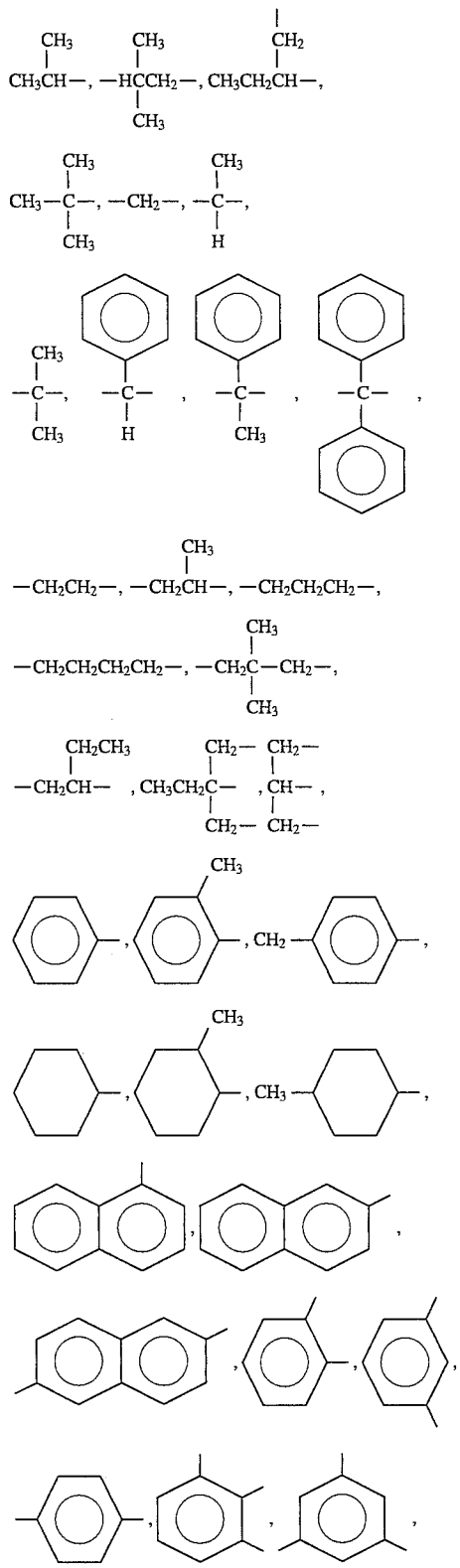
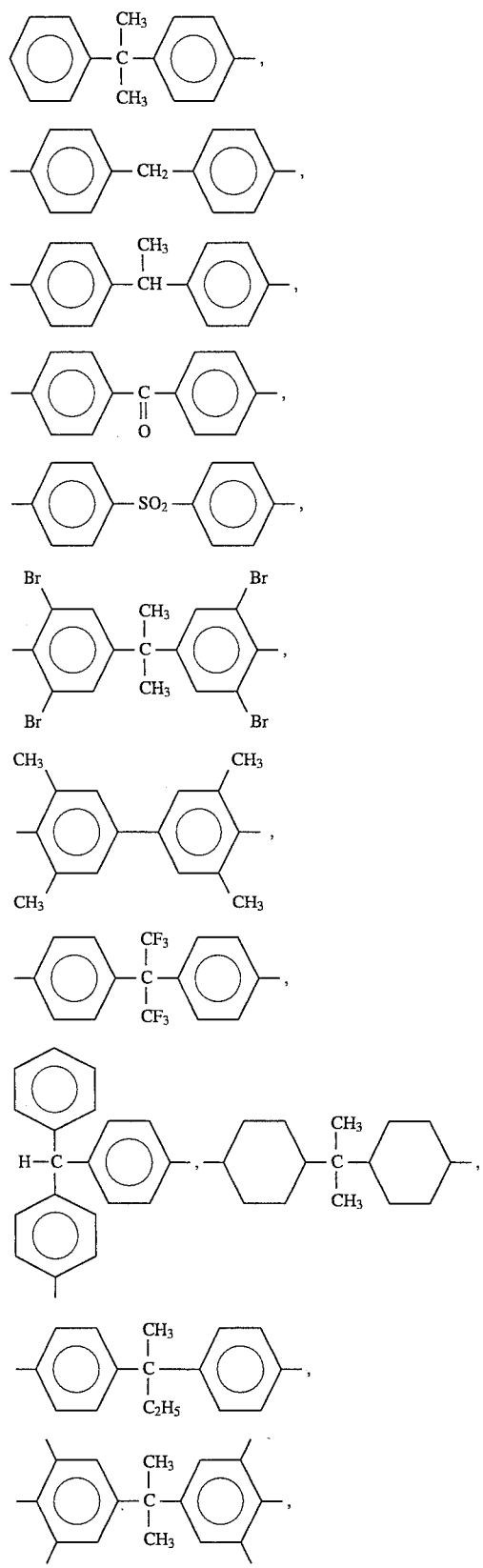

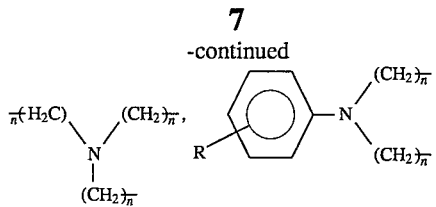

(wherein n is an integer of 2 to 10.). Among them, the following groups are preferable:

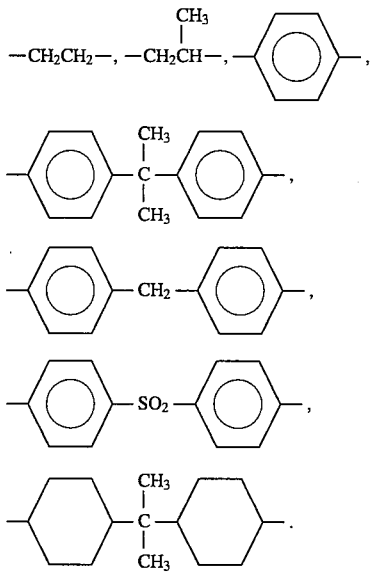

Another example of the curing agent is a compound having an ester linkage of the formula:

$$(X-R^2-O-\underset{\underset{O}{\|}}{C})_a R^4 \quad (IV)$$

wherein X is a group having at least one hydrosilyl group, $R^2$ is a divalent hydrocarbon group having 2 to 20 carbon atoms which may have at least one ether linkage, $R^4$ is an organic group having 1 to 30 carbon atoms, and a is an integer of 1 to 4.

In the formula (IV), $R^2$ is the same as $R^2$ in the formula (III). $R^4$ is a mono-, di-, tri-, tetra-valent organic aromatic or aliphatic group having 1 to 30 carbon atoms. Specific examples of $R^4$ are $CH_3-$, $CH_3CH_2-$, $CH_3CH_2CH_2-$, $-(CH_2)_2-$, $-(CH_2)_3-$, $-(CH_2)_4-$, $-(CH_2)_5-$, $-(CH_2)_6-$, $-(CH_2)_7-$,

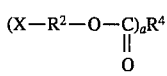

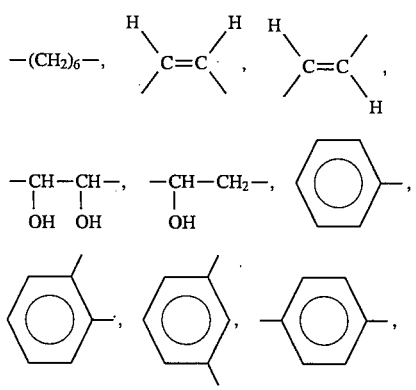

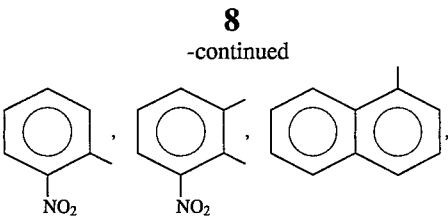

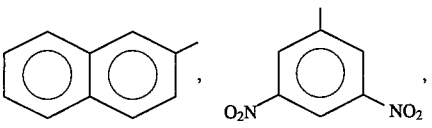

$CH_3CH_2CHCH-$, $CH_3CH=CHCH-$,

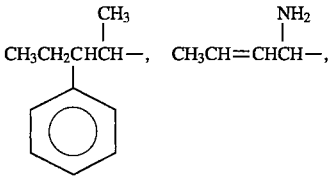

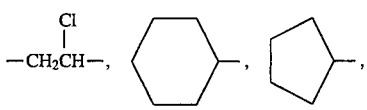

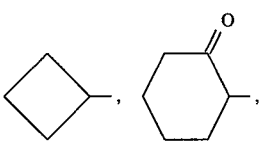

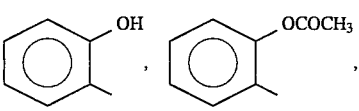

$CH_3(CH_2)_7CH=CH(CH_2)_7-$, 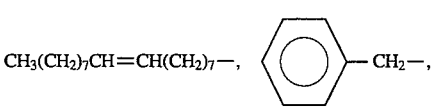

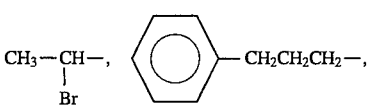

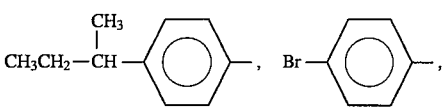

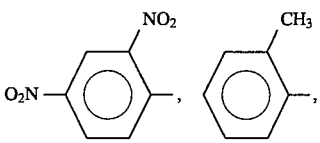

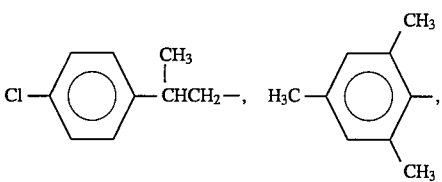

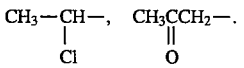

Among them, the following groups are preferable:
$-(CH_2)_2-$, $-(CH_2)_3-$, $-(CH_2)_6-$,

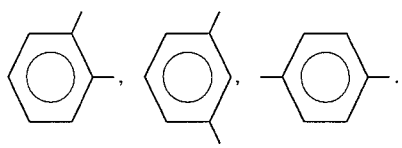

A further example of the curing agent is a compound having a hydrocarbon backbone of the formula:

$$X_a R^5 \quad (V)$$

wherein X is a group having at least one hydrosilyl group, $R^5$ is a mono-, di-, tri- or tetra-valent hydrocarbon group having 2 to 50 carbon atoms, and a is an integer of 1 to 4.

In the formula (V), $R^5$ represents a mono-, di-, tri-, or tetra-valent hydrocarbon group having 2 to 50 carbon atoms. Specific examples of $R^5$ are $CH_3(CH_2)_n$— (n=1 to 10), $(CH_3)_2CHCH_2$—,

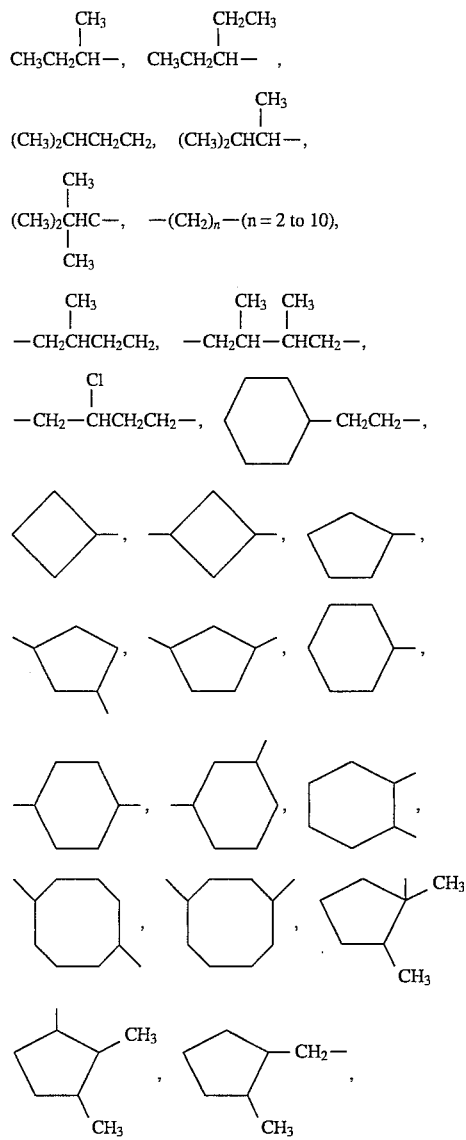

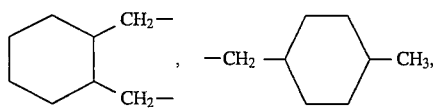

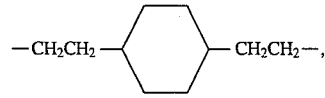

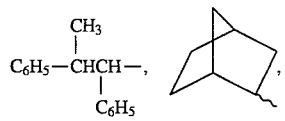

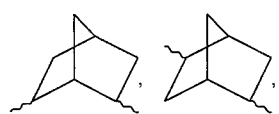

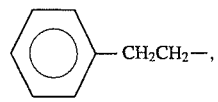

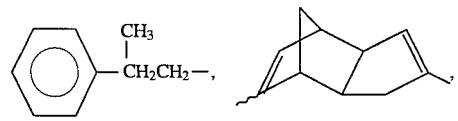

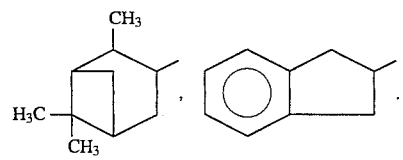

Among them, the following groups are preferable:
—$(CH_2)_n$— (n=2 to 10),

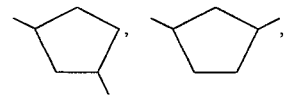

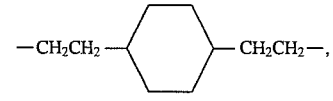

Further, —$(CH_2)_n$— (n=2 to 10) is particularly preferable.

Yet further example of the organic curing agent having the hydrosilyl group according to the present invention is a compound having a carbonate linkage of the formula:

$$(X-R^2-OCO)_a R^6 \quad (VI)$$

wherein X is a group having at least one hydrosilyl group, $R^2$ is a divalent hydrocarbon group having 2 to 20 carbon atoms which may have at least one ether linkage, $R^6$ is a mono-, di-, tri- or tetra-valent organic group, and a is an integer of 1 to 4.

In the formula (VI), $R^2$ is the same as $R^2$ in the formulas (III) and (IV). Specific examples of $R^6$ are $CH_3-$, $CH_3CH_2-$, $CH_3CH_2CH_2-$,

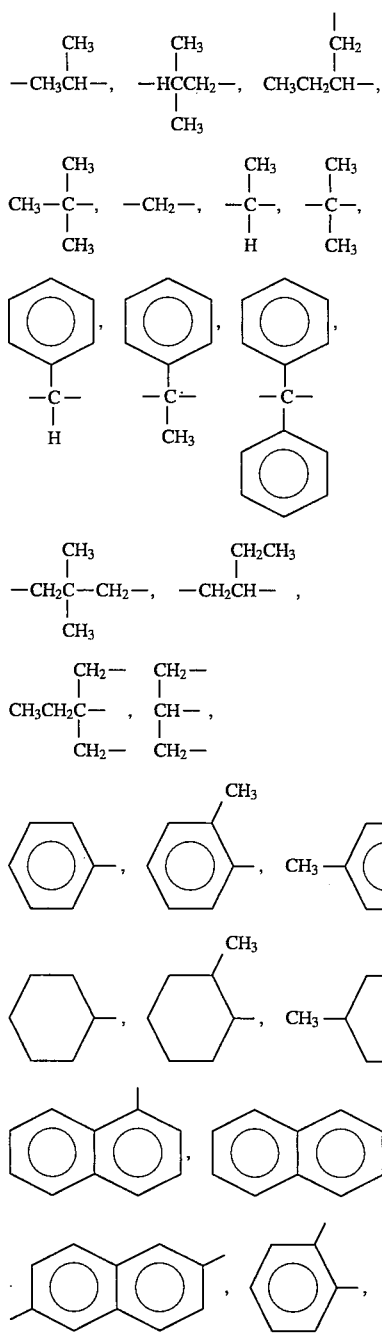

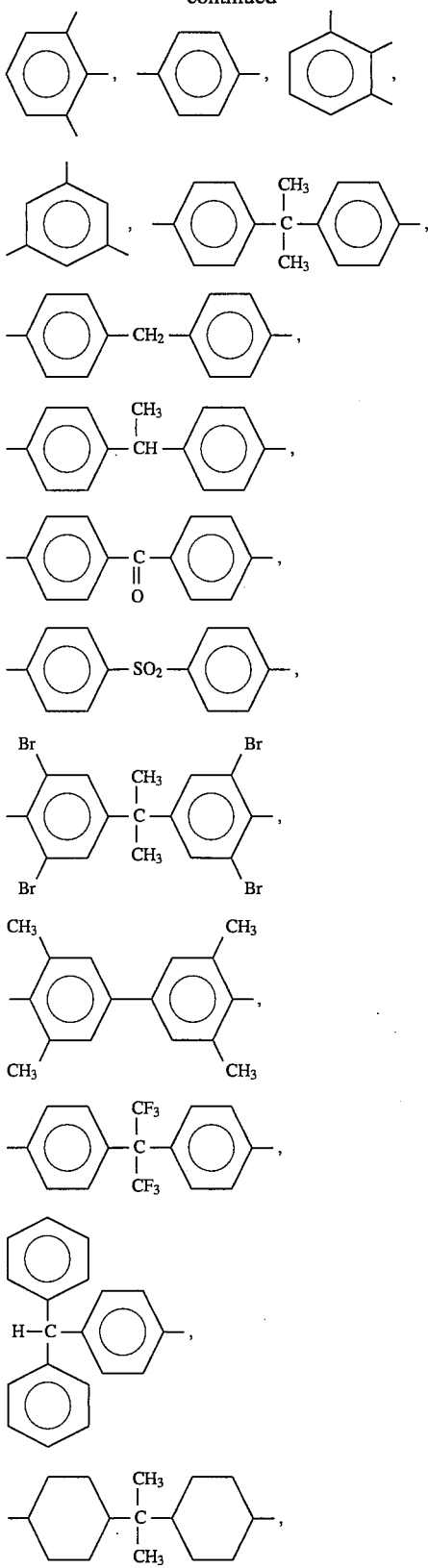

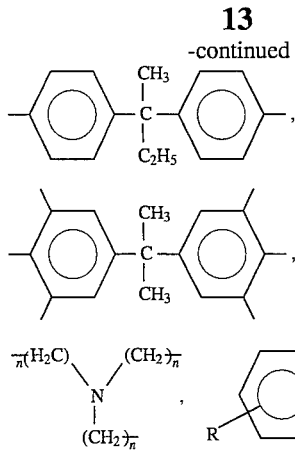

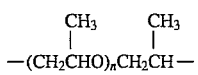

(wherein n is an integer of 2 to 10.),
—(CH$_2$CH$_2$O)$_n$CH$_2$CH$_2$— (wherein n is an integer of 1 to 5.),

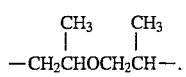

(wherein n is an integer of 1 to 5.),
—(CH$_2$CH$_2$CH$_2$O)$_n$CH$_2$CH$_2$CH$_2$— (wherein n is an integer of 1 to 5.), and —(CH$_2$CH$_2$CH$_2$CH$_2$O)$_n$CH$_2$CH$_2$CH$_2$CH$_2$— (wherein n is an integer of 1 to 5.).

Among them, the following groups are particularly preferable: —CH$_2$CH$_2$OCH$_2$CH$_2$—, —CH$_2$CH$_2$OCH$_2$CH$_2$OCH$_2$CH$_2$—, and $$-CH_2\overset{CH_3}{\underset{|}{C}H}OCH_2\overset{CH_3}{\underset{|}{C}H}-.$$

A method for preparing the hydrosilyl group-containing organic curing agent according to the present invention is not limited and is arbitrary. For example, the following methods are contemplated: (i) a method which comprises reducing an Si—Cl group to an Si—H group in an organic compound having the Si—Cl group in the molecule by treating the organic compound with a reducing agent such as LiAlH$_4$ or NaBH$_4$, (ii) a method which comprises reacting an organic compound having a functional group X in the molecule with a compound having a hydrosilyl group and a functional group Y which reacts with the functional group X, and (iii) a method which comprises retaining hydrosilyl groups in the molecule of an organic compound after a selective hydrosilylation reaction of the organic compound having an alkenyl group with a polyhydrosilane compound having at least two hydrosilyl groups.

The second aspect of the present invention resides in the above method (iii) for preparing the hydrosilyl group-containing organic curing agent. Namely, the present invention relates to a method for preparing an organic curing agent having at least two hydrosilyl groups in a molecule which is not a polymer, which method comprises reacting (A) an organic compound having at least one alkenyl group in a molecule with (B) a polyvalent hydrogensilicon compound in the presence of a hydrosilylation catalyst so that the hydrosilyl groups remain after the reaction.

Various ether compounds, ester compounds, hydrocarbon compounds and carbonate compounds having an alkenyl group can be used as the component (A).

The ether compound used as the component (A) is not limited and it is a compound which has an alkenyl ether group. An example of such compound is a compound having an ether linkage of the formula:

wherein R$^7$ is a hydrocarbon group having 0 to 18 carbon atoms which may have at least one ether linkage, R$^8$ is hydrogen or a methyl group, R$^3$ is an organic group having 1 to 30 carbon atoms, and a is an integer of 1 to 4. In the formula (VII), R$^7$ represents the divalent hydrocarbon group having 0 to 18 carbon atoms, and at least one ether linkage may be present in R$^7$. Specific examples of R$^7$ are —CH$_2$—, —CH$_2$CH$_2$—, —CH$_2$CH$_2$CH$_2$—,

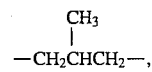

—CH$_2$CH$_2$CH$_2$CH$_2$—, —CH$_2$CH$_2$O—CH$_2$CH$_2$— and —CH$_2$CH$_2$O—CH$_2$CH$_2$CH$_2$—. —CH$_2$— is preferable because of the easiness of its preparation. In the formula (VII), R$^3$ is a mono-, di-, tri- or tetra-valent organic aromatic or aliphatic group having 1 to 30 carbon atoms and it is the same as R$^3$ in the formula (III).

Another example of the component (A) is a compound having an ester linkage of the formula:

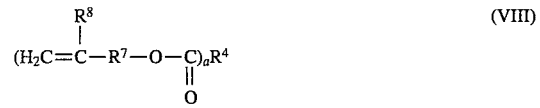

wherein R$^7$ is a hydrocarbon group having 0 to 18 carbon atoms which may have at least one ether linkage, R$^8$ is hydrogen or a methyl group, R$^4$ is an organic group having 1 to 30 carbon atoms, and a is an integer of 1 to 4.

In the formula (VIII), R$^7$ is the same as R$^7$ in the formula (VII) and R$^4$ is the same as R$^4$ in the formula (IV).

Further example of the component (A) is a compound having a hydrocarbon backbone of the formula:

wherein R$^8$ is hydrogen or a methyl group, R$^5$ is a mono-, di-, tri- or tetra-valent hydrocarbon group having 2 to 50 carbon atoms, and a is an integer of 1 to 4. In the formula (IX), R$^5$ is the same as R$^5$ in the formula (V).

Yet further example of the component (A) is a compound having a carbonate linkage of the formula:

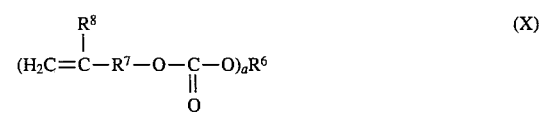

wherein R$^7$ is a hydrocarbon group having 0 to 18 carbon atoms which may have at least one ether linkage, R$^8$ is hydrogen or a methyl group, R$^6$ is an organic group having 1 to 30 carbon atoms, and a is an integer of 1 to 4.

In the formula (X), R$^7$ is the same as R$^7$ in the formula (VII) and R$^6$ is the same as R$^6$ in the formula (VI).

Specific examples of the polyvalent hydrogensilicon compound (B) used according to the present invention are a monosilane compound such as (CH$_3$)$_2$SiH$_2$, (C$_6$H$_5$)$_2$SiH$_2$, CH$_3$SiH$_3$, C$_6$H$_5$SiH$_3$, (C$_2$H$_5$)$_2$SiH$_2$ and CH$_3$(CH$_2$)$_5$SiH$_3$; a polysilicon compound such as H(CH$_3$)$_2$SiSi(CH$_3$)$_2$H, H(CH$_3$)$_2$SiCH$_2$CH$_2$Si(CH$_3$)$_2$H,

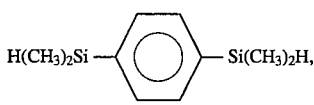

H(CH$_3$)$_2$SiSi(CH$_3$)H$_2$, H(CH$_3$)$_2$SiNHSi(CH$_3$)$_2$H, [H(CH$_3$)$_2$Si]$_3$N and H(CH$_3$)$_2$SiOC(CH$_3$)=NSi(CH$_3$)$_2$H; and various linear, branched and cyclic polyvalent hydrogen polysiloxanes such as

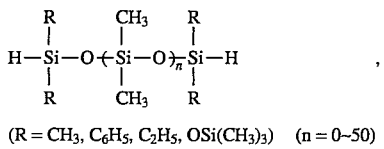

(R = CH$_3$, C$_6$H$_5$, C$_2$H$_5$, OSi(CH$_3$)$_3$)   (n = 0~50)

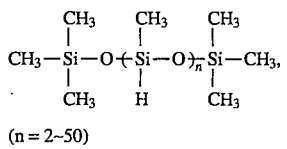

(n = 2~50)

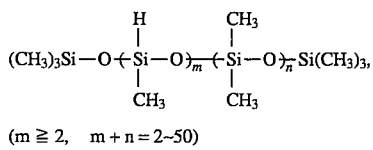

(m ≧ 2,  m + n = 2~50)

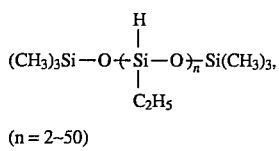

(n = 2~50)

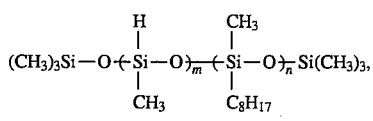

(m ≧ 2,  m + n = 3~50)

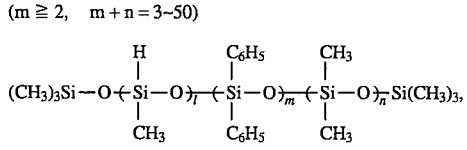

(l ≧ 2,  l + m + n = 3~50)

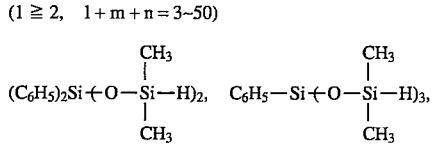

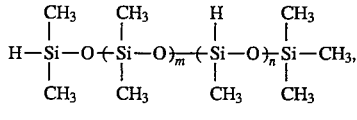

(n ≧ 2,  m + n = 3~50)

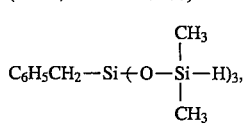

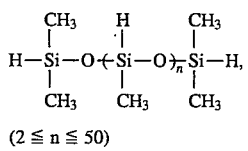

(2 ≦ n ≦ 50)

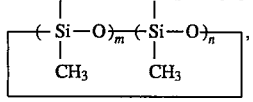

(m + n = 3~6,  m ≧ 2)

RSi[OSi(CH$_3$)$_2$H]$_3$   (R = CH$_3$, C$_6$H$_5$, C$_2$H$_5$),

Si[OSi(CH$_3$)$_2$H]$_4$,

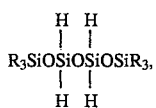

(R = CH$_3$, C$_6$H$_5$, C$_2$H$_5$),

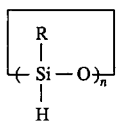

(n = 3~20)   (R = CH$_3$, C$_6$H$_5$, C$_2$H$_5$)

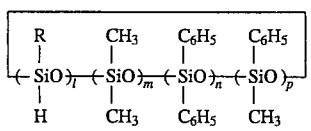

(l ≧ 2, p + l + m + n = 3~20   R = CH$_3$, C$_2$H$_5$, C$_6$H$_5$)

The number of hydrosilyl groups in one molecule of the polyvalent hydrogensilicon compound (B) is preferably 2 to 16, particularly 3 to 13. The polyvalent hydrogensilicon compound (B) preferably has a molecular weight of lower than 500, so that the hydrosilyl group-containing organic curing agent according to the present invention prepared from the component (A) and the component (B) does not deteriorate compatibility. The following polyvalent hydrogensilicon compounds (B) are particularly preferable because of their high reactivity toward a hydrosilylation reaction with the component (A):

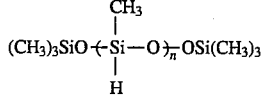

(n = 3~5)

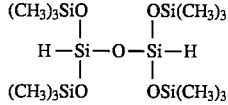

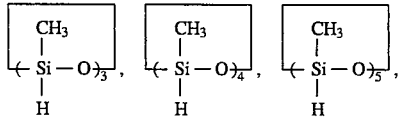

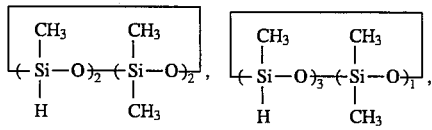

-continued

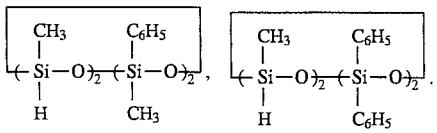

Since unreacted components can be easily removed under a reduced pressure after the hydrosilylation reaction, the following compounds are particularly preferable:

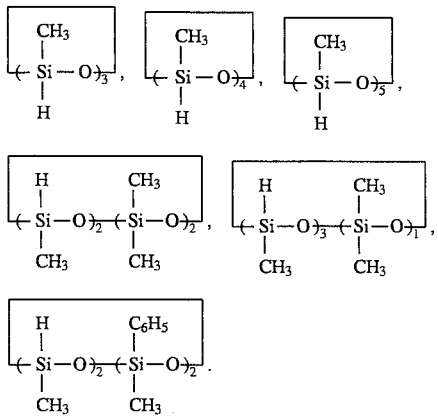

The hydrosilyl group-containing organic curing agent according to the present invention can be prepared by the hydrosilylation reaction of the alkenyl group-containing organic compound (A) and the polyvalent hydrogensilicon compound (B). Specific examples of a catalyst used for the reaction are platinum metal; solid platinum supported on a carrier such as alumina, silica or carbon black; chloroplatinic acid; a complex of chloroplatinic acid with an alcohol, an aldehyde or a ketone; a platinum-olefin complex (for example, $Pt(CH_2=CH_2)_2(PPh_3)_2 Pt(CH_2=CH_2)_2Cl_2)$; a platinum-vinylsiloxane complex (for example, $Pt_n(ViMe_2SiOSiMe_2Vi)_m$, $Pt[(MeViSiO)_4]_m$); a platinum-phosphine complex (for example, $Pt(PPh_3)_4$, $Pt(PBu_3)_4$); a platinum-phosphite complex (for example, $Pt[P(OPh)_3]_4$, $Pt[P(OBu)_3]_4$) (wherein Me is a methyl group, Bu is a butyl group, Vi is a vinyl group, Ph is a phenyl group and m are an integer.); dicarbonyldichloroplatinum; a platinum-hydrocarbon complex described in U.S. Pat. Nos. 3,159,601 and 3,159,662 to Ashby; and a platinum alcoholate catalyst described in U.S. Pat. No. 3,220,972 to Lamoreaux. In addition, a chloroplatinum-olefin complex described in U.S. Pat. No. 3,516,946 to Modic is also useful in the present invention.

Specific examples of the catalyst other than the platinum compounds are $RhCl(PPh_3)_3$, $RhCl_3$, $Rh/Al_2O_3$, $RuCl_3$, $IrCl_3$, $FeCl_3$, $AlCl_3$, $PdCl_2 \cdot 2H_2O$, $NiCl_2$ and $TiCl_4$ (wherein Ph is a phenyl group.). Only one catalyst or a combination of at least two catalysts may be used. In view of catalytic activity, chloroplatinic acid, the platinum-olefin complex, the platinum-vinylsiloxane complex and the like are preferable. An amount of the catalyst is not limited, but $10^{-1}$ to $10^{-8}$ mol, based on one mol of the alkenyl group of the component (A), may be used. The range between $10^{-3}$ and $10^{-6}$ mol is preferable.

The use of a solvent is not necessarily required in the hydrosilylation reaction. An inert organic solvent may be used when the starting materials are solid or have a high viscosity and it is difficult to carry out an operation such as stirring. Specific examples of the inert organic solvents are aromatic hydrocarbon solvents such as benzene, toluene and xylene; aliphatic hydrocarbon solvents such as hexane and octane; ether solvents such as ethyl ether and butyl ether; ketone solvents such as methyl ethyl ketone; and halogenated hydrocarbon solvents such as trichloroethylene.

A manner for adding the component (A), the component (B) and the hydrosilylation catalyst is not limited and includes charging three components simultaneously, adding the component (A) and the hydrosilylation catalyst to the component (B), adding the component (B) to the component (A) and the hydrosilylation catalyst, adding the component (A) to the component (B) and the catalyst, and adding each component simultaneously. In order to carry out the reaction so that the hydrosilyl groups remain after the reaction, preferably the polyvalent hydrogensilicon compound (B) is always present in excess to the component (A). Therefore, it is preferable to add a mixture of the alkenyl group-containing organic compound (A) and the hydrosilylation catalyst to the polyvalent hydrogensilicon compound (B). The reaction temperature may be from 0° to 200° C., preferably from 50° to 150° C. When the reaction temperature is lower than 0° C., a catalyst activity is insufficient and therefore a reaction rate is low. When it is higher than 200° C., the catalyst is often deactivated.

Since the hydrosilyl group-containing organic curing agent prepared by the above method usually contains the hydrosilylation catalyst after the reaction, its stability is generally poor. When the curing agent is kept standing for a long time or exposed to the moisture, an Si—H group converts to an Si—OH group and a phenomenon such as a viscosity increase or a gelation is observed. Therefore, the catalyst is preferably removed from the polymer after the hydrosilylation reaction. Specific examples for a method for removing the catalyst are a method which comprises mixing a reaction solution with silica, silica gel, an ion exchange resin or the like or treating the reaction solution with a column comprising the same, and a method which comprises washing a reaction mixture with a neutral or weakly acidic aqueous solution.

The hydrosilyl group-containing organic curing agent prepared in this manner generally has better compatibility with an organic polymer, in comparison with known hydrosilyl group-containing polysiloxanes. When the hydrosilyl group-containing organic curing agent according to the present invention is mixed with various alkenyl group-containing organic polymers in the presence of said various hydrosilylation catalysts and then cured, a homogeneous cured material can be obtained without a phenomenon such as foaming since these two components have good compatibility. The curing conditions are not limited. In general, the curing can be carried out at 0° to 200° C., preferably 50° to 150° C. for 10 seconds to 4 hours. At a high temperature of 80° to 150° C., the curing is sometimes completed for a short time of 10 seconds to 30 minutes. For example, even if the cured material prepared according to said method has a thickness of at least 1 cm, the homogeneously cured material having good depth curability can be obtained. Properties of the cured material depend on the molecular structure and the molecular weight of the curing agent and the organic polymer and the like. A rubbery material to a resinous material can be prepared.

When the cured material is prepared, various solvents, plasticizers, fillers, pot-life extending agents, pigments, age resistors, ultraviolet light absorbers and adhesives can be used in addition to three main components of the hydrosilylation catalyst, the hydrosilyl group-containing curing agent and the alkenyl group-containing organic polymer.

The third aspect of the present invention resides in a curable composition which comprises (C) an organic curing agent having at least two hydrosilyl groups in a molecule, which is not a polymer, (D) an organic polymer having at least one alkenyl group in a molecule, and (E) a hydrosilylation catalyst.

Various hydrosilyl group-containing ether, ester, hydrocarbon and carbonate curing agents which are described in connection with the first aspect can be used as the organic curing agent (C) having at least two hydrosilyl groups in a molecule. Preferable molecular weight and molecular structure of the curing agent, preferable structure of the hydrosilyl group, and the preferable number of the hydrosilyl groups per one molecule are the same as those made in the explanation of the first aspect. A method for preparing the component (C) is not limited, but the method of the second aspect is preferable.

The organic polymer having at least one alkenyl group in a molecule (D) is not limited, and it may have various polymer chains.

Specific examples of the polymer chain in the component (D) are a polyether polymer such as polyoxyethylene, polyoxypropylene, polyoxytetramethylene, polyoxyethylene-polyoxypropylene; a polyester polymer prepared by a condensation of a dibasic acid such as adipic acid and a glycol or by a ring-opening polymerization of lactones; ethylene-propylene copolymer; polyisobutylene; a copolymer of isobutylene with isoprene or the like; polychloroprene; polyisoprene; a copolymer of isoprene with butadiene, acrylonitrile, styrene or the like; polybutadiene; a copolymer of butadiene with styrene, acrylonitrile or the like; a polyolefin polymer prepared by hydrogenating polyisoprene, polybutadiene, or a copolymer of isoprene or butadiene with acrylonitrile, styrene or the like; a polyacrylate ester prepared by a radical polymerization of a monomer such as ethyl acrylate, butyl acrylate or the like; an acrylate ester copolymer of an acrylate ester such as ethyl acrylate or butyl acrylate with vinyl acetate, acrylonitrile, methyl methacrylate, styrene or the like; a graft polymer prepared by polymerizing a vinyl monomer in said organic polymer; polysulfide polymer; a polyamide polymer, for example, nylon 6 prepared by a ring opening polymerization of ε-aminocaprolactam, nylon 66 prepared by a polycondensation of hexamethylenediamine and adipic acid, nylon 610 prepared by a polycondensation of hexamethylenediamine and sebacic acid, nylon 11 prepared by a polycondensation of ε-aminoundecanoic acid, nylon 12 prepared by a ring opening polymerization of ε-aminolauric lactam, a copolymerized nylon containing at least two components of said nylon; polycarbonate polymer, for example, prepared by a polycondensation of bisphenol A and carbonyl chloride; and a diallyl phthalate polymer.

Among the polymers having the above polymer chains, the polyether polymer, the acrylate ester polymer, the polyester polymer, the hydrocarbon polymer and the polycarbonate polymer are preferable since they have good compatibility with the hydrosilyl group-containing organic curing agent (C). In particular, the case in which the component (C) is the ether curing agent and the component (D) is the polyether polymer, the case in which the component (C) is the ester curing agent and the component (D) is the polyester polymer, and the case in which the component (C) is the hydrocarbon curing agent and the component (D) is the hydrocarbon polymer are preferable.

The alkenyl group in the component (D) is not limited and the preferable alkenyl group is of the formula:

(XI)

wherein $R^1$ is hydrogen or a methyl group.

A method for introducing the alkenyl group into the organic polymer (D) may be a conventionally proposed method and is roughly classified in a method for introducing the alkenyl group after the polymerization and a method for introducing the alkenyl group during the polymerization.

The method for introducing the alkenyl group after the polymerization includes, for example, a method comprising reacting an organic polymer having a functional group such as a hydroxyl group or an alkoxide group at the molecular end, in the main chain or in the side chain, with an organic compound having an alkenyl group and an active group which is reactive to said functional group so as to introduce the alkenyl group at the molecular end, in the main chain or in the side chain. Specific examples of the organic compound having the alkenyl group and the active group which is reactive to said functional group are a $C_3$–$C_{20}$ unsaturated aliphatic acid, acid halide and acid anhydride such as acrylic acid, methacrylic acid, vinyl acetate, acrylic chloride and acrylic bromide: a $C_3$–$C_{20}$ unsaturated aliphatic acid substituted halide such as allyl chloroformate ($CH_2$=$CHCH_2OCOCl$) and allyl bromoformate ($CH_2$=$CHCH_2OCOBr$); allyl chloride, allyl bromide, vinyl(chloromethyl)benzene, allyl(chloromethyl)benzene, allyl(bromomethyl)benzene, allyl chloromethyl ether, allyl-(chloromethoxy)benzene, 1-butenyl chloromethyl ether, 1-hexenyl(chloromethoxy)benzene and allyloxy(chloromethyl)benzene.

The method for introducing the alkenyl group during the polymerization includes, for example, a method comprising introducing the alkenyl group in the main chain or at the molecular end of the polymer by using a vinyl monomer which has an alkenyl group having a low radical reactivity in the molecule such as allyl methacrylate and allyl acrylate, or a radical chain transfer agent which has an alkenyl group having a low radical reactivity such as allyl mercaptan when the organic polymer (D) is prepared by a radical polymerization. When a rubbery cured material is prepared by using the composition according to the present invention, the alkenyl group at the molecular end in the component (D) is preferable since an effective network chain length of the cured material is elongated.

A bonding manner of the alkenyl group and the main chain of the organic polymer is not limited. The alkenyl group may directly bond to the main chain of the organic polymer by a carbon-carbon linkage, or it may bond to the main chain of the polymer through an ether, ester, carbonate, amide or urethane linkage.

A molecular weight of the component (D) is preferably from 500 to 50,000, more preferably from 500 to 20,000 in view of the properties of the cured material and the compatibility with the component (C). The number of the alkenyl groups present in one molecule is preferably from 2 to 5 on the average.

The molar ratio of the hydrosilyl group to the alkenyl group in the components (C) and (D) is preferably from 0.2 to 5.0, more preferably from 0.4 to 2.5. When the molar ratio is smaller than 0.2, the curing is insufficient and only a sticky cured material having low strength is obtained. When the molar ratio is larger than 5.0, the cracking and voids often occur and a homogeneous cured material having high strength cannot be obtained since many active hydrosilyl groups remain in the cured material after the curing.

The hydrosilylation catalyst (E) according to the present invention is not limited and is arbitrary. Concretely, the same catalyst as used in the preparation of the hydrosilyl group-containing organic curing agent according to the second aspect of the present invention can be used. One of these catalysts may be used or a combination of at least two of these catalysts may be used. Chloroplatinic acid, a platinum-olefin complex and a platinum-vinylsiloxane complex are preferable in view of the catalyst activity. A catalyst amount is not limited, but it is preferably from $10^{-1}$ to $10^{-8}$ mol based on 1 mol of the alkenyl group of the component (D). $10^{-3}$ to $10^{-6}$ mol is more preferable.

The homogeneous cured material having good depth curability without a phenomenon such as the foaming can be obtained by mixing the components (C), (D) and (E) and effecting the curing. Curing conditions are not limited, but the curing is generally carried out at 0° to 200° C., preferably 30° to 150° C. for 10 seconds to 4 hours. In particular, at a high temperature of 80° to 150° C., the curing is sometimes completed for a short time of 10 seconds to 1 hour. Properties of the cured material depend on the molecular structure and the molecular weight of the components (C) and (D), and a rubbery material to a resinous material can be prepared.

When the cured material is prepared, various solvents, adhesion improving agents, property controlling agents, preservation stability improving agents, plasticizers, fillers, age resistors, ultraviolet light absorbers, metal inactivating agents, antiozonants, light stabilizers, amine-based radical chain inhibiting agents, phosphorus-based peroxide decomposers, lubricants, pigments, foaming agents and the like can suitably be added according to the desired application in addition to the three essential components (C), (D) and (E).

EXAMPLES

The present invention is explained with referring the following Examples, but it is not limited to the Examples.

Preparative Example 1

Bisphenol A (114 g, 0.5 mol), 5N aqueous solution of sodium hydroxide (250 ml, 1.25 mol) and deionized water (575 ml) were intimately mixed. Then, a phase transfer catalyst of benzyltriethylammonium chloride:

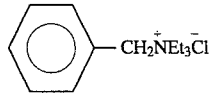

(7.78 g, 25 mmol) was added. A solution of allyl bromide (242 g, 2.0 mol) in toluene (300 ml) was slowly dropwise added from a dropping funnel to said solution. The reaction was carried out at 80° C. for two hours while stirring. A pH of an aqueous layer was measured. Since the aqueous layer was acidic, the heating and the stirring were stopped. After the organic layer was washed with an aqueous solution of sodium bicarbonate, it was further washed with deionized water and dried with $Na_2SO_4$. A volatile was removed by an evaporation, and a residue was dried at 80° C. under a reduced pressure for two hours to obtain a pale yellow viscous liquid (146 g). Yield: 95%. According to an elemental analysis, 300 MHz $^1H$ NMR and IR spectra, the viscous liquid was confirmed to be diallyl ether of bisphenol A:

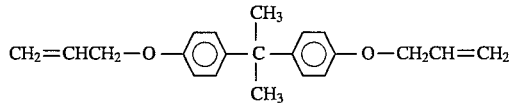

IR (neat, $cm^{-1}$): 3070 (m, $v_{=C-H}$), 3030 (m), 2960 (s), 2920 (s), 2860 (s, $v_{C-H}$), 1645 (m, $v_{C=C}$), 1620 (s), 1520 (s), 1290 (s), 1235 (s), 1180 (s), 1025 (s), 1000 (s), 920 (s), 825 (s).

$^1H$ NMR (300 MHz): see FIG. 1.

Elemental analysis Calcd.: C, 81.78%; H, 7.84%. Found: C, 81.9%; H, 7.96%.

Preparative Example 2

Polyoxypropylene having an allyl-type olefin group at a molecular end was prepared according to a method disclosed in Japanese Patent Kokai Publication No. 134095/1978. Polyoxypropylene glycol having an average molecular weight of 3,000 and sodium hydroxide powder were mixed at 60° C., and bromochloromethane was added to carry out the reaction and increase the molecular weight. Then, allyl chloride was added to etherify the molecular end with the allyl group at 110° C. This was treated with aluminum silicate to prepare purified allyl ether-terminated polyoxypropylene.

This polyether had an average molecular weight of 7,960 and 92% of the terminal groups were olefin groups (0.0231 mol/100 g) according to an iodine value. A viscosity measured by an E-type viscometer was 130 poises (40° C.).

Preparative Example 3

A one liter four-necked flask equipped with a stirring rod, a dropping funnel, a thermometer, a three-way cock and a condenser was used. Hydroxyl group-terminated polytetramethylene oxide having an average molecular weight of about 2,000 (trade name: Terathane 2000, manufactured by du Pont) (300 g) was charged in the flask. Azeotropic deaeration was carried out by using toluene, and then a solution of t-BuOK (50.5 g) in THF (200 ml) was added. After the mixture was stirred at 50° C. for one hour, allyl chloride (49 ml) was added from the dropping funnel over one hour. After the addition was completed, the mixture was reacted at 50° C. for about one hour. Then, aluminum silicate (30 g) was added at a room temperature, and stirred for thirty minutes. The mixture was filtered with a filter aid of diatomaceous earth, and volatile components were removed by an evaporation to obtain a transparent viscous liquid (about 230 g). The product was kept standing at a room temperature over a night and it crystallized to form a white solid. An iodometric titration (0.0718 mol/100 g) confirmed that the allyl group was introduced at 73% of molecular ends of polytetramethylene oxide.

Preparative Example 4

To hydrogenated polyisoprene having a hydroxy group at both ends (Epol (trade name) manufactured by Idemitsu Sekiyu Kagaku Kabushiki Kaisha) (300 g), toluene (50 ml) was added and the dehydration was curried out with azeotropy. A solution of t-BuOK (48 g) in THF (200 ml) was injected. After the reaction was carried out at 50° C. for 1 hour, allyl chloride (47 ml) was dropwise added over about 30 minutes. After the addition was completed, the reaction was carried out at 50° C. for 1 hour. After the reaction was completed, aluminum silicate (30 g) was added to the reaction solution so as to absorb a resulted salt and then the mixture was stirred at a room temperature for 30 minutes. Through filtration and purification, allyl-terminated hydrogenated polyisoprene (about 250 g) was obtained as a viscous liquid. A 300 MHz $^1H$ NMR analysis confirmed that the allyl group was introduced at 92% of the molecular ends. The molar number of the olefin determined according to an iodine value was 0.1046 mol/100 g. A viscosity according to an E-type viscometer was 302 poises (23° C.).

Typical properties of Epol (from a technical brochure)

| | |
|---|---|
| Hydroxy group content (meq/g) | 0.90 |
| Viscosity (poise/30° C.) | 700 |
| Average molecular weight (measured by VPO) | 2,500 |

Preparative Example 5

A toluene solution of acrylate ester monomers which consists of n-butyl acrylate (115.72 g), methyl methacrylate (60.00 g), allyl methacrylate (20.16 g), n-dodecyl mercaptan (6.46 g), azobisisobutyronitrile (2.0 g) and toluene (400 ml) was dropwise added from a dropping funnel to a flask which contains refluxed toluene (50 ml) under a nitrogen atmosphere. After the addition was completed, the mixture was further reacted for two hours. The reacted solution was evaporated and dried under a reduced pressure at 80° C. for three hours to obtain a pale yellow viscous liquid oligomer (about 195 g). The molar number of the allyl group in the oligomer was 0.0818 mol/100 g according to an iodometric titration and a molecular weight of the oligomer was 2,950 according to a VPO. It was revealed that 2.4 allyl groups on the average were introduced in one molecule.

Preparative Example 6

In a round-bottom flask equipped with a stirring rod, a thermometer, a dropping funnel, a nitrogen introducing tube and a condenser, hydroxy group-terminated polycaprolactone (a number average molecular weight: 3,000, a hydroxy group equivalent: 1,500) (300 g, 0.1 mol), pyridine (24.0 g) and THF (300 ml) were charged. Allyl chloroformate (32 g) was slowly dropwise added from the dropping funnel at a room temperature. Then, the mixture was heated to 50° C. and stirred for 3 hours. After a resulted salt was removed by filtration, toluene (150 ml) was added and the mixture was washed with aqueous hydrochloric acid (200 ml) and neutralized and condensed to obtain allyl-terminated polycaprolactone. The resulted oligomer had a number average molecular weight of 3,200 according to a VPO measurement. A 300 MHz NMR of an olefin portion confirmed the introduction of the allyl group. The quantification of the olefin by an iodometric titration (0.0573 mol/100 g) confirmed that the number of allyl-type unsaturated groups introduced in one molecule was 1.83 on the average.

Example 1

A 200 ml four-necked flask equipped with a stirring rod, a dropping funnel, a thermometer, a three-way cock and a condenser was used. In the flask, a cyclic hydrogenpolysiloxane:

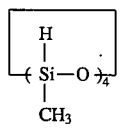

(LS 8600 manufactured by Shin-Etsu Chemical Co., Ltd.) (12.03 g, 50 mmol) and toluene (20 ml) were charged under a nitrogen atmosphere. After bisphenol A diallyl ether (6.16 g, 20 mmol) prepared in Preparative Example 1 and a solution of chloroplatinic acid catalyst (a solution in which $H_2PtCl_6 \cdot 6H_2O$ (1.0 g) is dissolved in ethanol/1,2-dimethoxyethane (⅑ v/v) (9 g)) (41 µl) were dissolved in toluene (50 ml) and intimately mixed, the toluene solution was charged in the dropping funnel. The toluene solution was dropwise added to the flask over 1.5 hours at 70° C. After the mixture was reacted at 80° C. for 5 hours, an IR spectra analysis was carried out. Since the complete disappearance of the olefin peak at 1645 $cm^{-1}$ was confirmed, the reaction was stopped. The reaction mixture was evaporated to remove volatile components. After hexane (100 ml) was added to the residue to fully dissolve the residue, the mixture was filtered to remove the catalyst. After hexane was distilled off under a reduced pressure, the residue was dried under a reduced pressure at 80° C. for one hour to obtain a pale yellow viscous liquid (12.0 g). Analysis such as 300 MHz $^1H$ NMR and IR spectra revealed that the viscous liquid is an ether curing agent having an Si—H group which has the following structure:

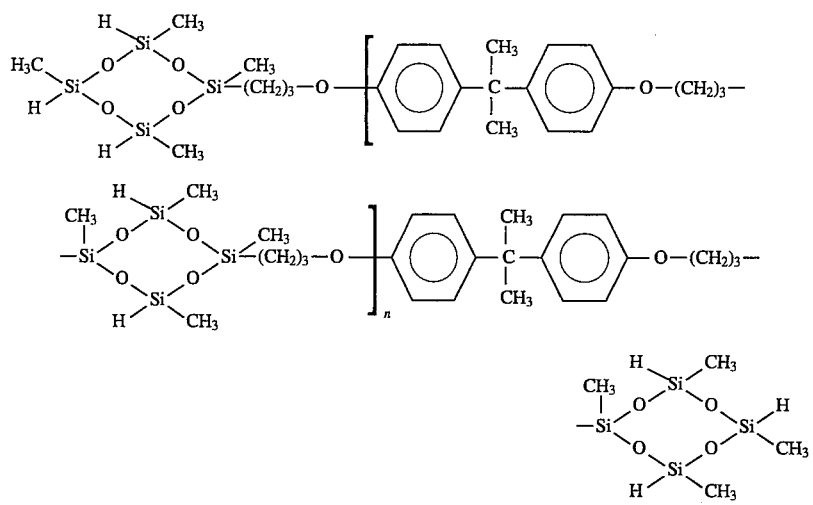

The measured proton intensity ratio (0.223) of Si—$\underline{H}$ to Si—$\underline{CH_3}$ according to 300 MHz $^1H$ NMR spectra was compared with the calculated proton intensity.
When n is 1:6/24=0.25
When n is 2:8/36=0.222

Figure 2:
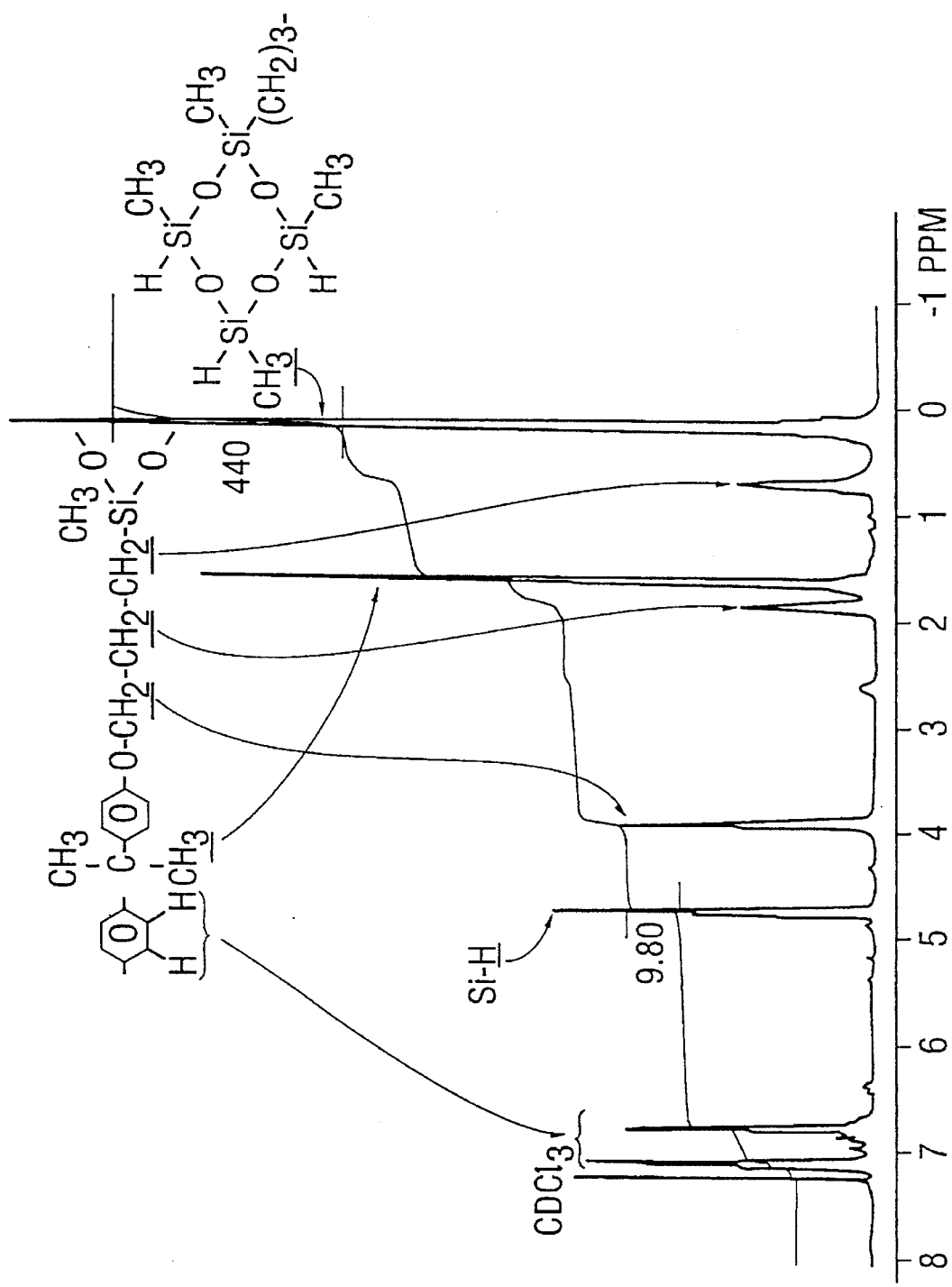
FIG. 2 is a 300 MHz $^1$H NMR spectrum chart of the Si—H group-containing ether curing agent obtained in Example 1.

The curing agent was a mixture consisting of, on the average, 4% of the compound (MW=789.4) wherein n is 0 and 96% of the compound (MW=1338.3) wherein n is 1. On the basis of this, the number of Si—H groups per a unit weight was calculated to be 0.604 mol/100 g. IR (neat, $cm^{-1}$): 3030 (w), 2960 (s), 2920 (s), 2860 (s), 2160 (s, $v_{Si-H}$), 1605 (m), 1505 (s), 1255 (s), 1070 (bs). $^1H$ NMR (300 MHz): see FIG. 2.

Example 2

The compatibility of an Si—H group-containing ether curing agent prepared in Example 1 with allyl group-containing organic polymers having various backbones was examined. According to combinations indicated in Table 1, the curing agent (an indicated amount) and the organic polymer (1.0 g) were intimately mixed and centrifugally defoamed. Then, the mixed state was observed. Although some mixtures were slightly opaque, mixtures were generally transparent and homogeneous. Said Si—H group-containing ether curing agent had good compatibility with various organic polymers.

For examining the curability, a solution (an indicated amount) in which a chloroplatinic acid catalyst solution used in Example 1 was diluted to a tenth concentration was added to each of said mixtures and intimately mixed. A part of the mixture was transferred on a gelation testing device (manufactured by Nisshin Kagaku Kabushiki Kaisha) and a snap-up time (the time which is required for forming a rubbery elastomer) was measured at an indicated temperature. Results are shown in Table 1. The compositions had a rapid curability at a high temperature.

homogeneous rubbery cured material having a thickness of about 3 mm. A No. 3 dumbbell test piece according to JIS K 6301 was punched off from the sheet of the cured material, and a tensile test was carried out at a pulling speed of 200 mm/min. Results are shown in Table 3.

Table 3 shows that a homogeneous rubbery cured material can be prepared by a short time cure when the hydrosilyl group-containing ether curing agent is used according to the present invention.

TABLE 1

Compatibility and curability of Si—H group-containing ether curing agent with allyl group-containing organic polymer

| | Allyl group-containing organic polymer | | | |
|---|---|---|---|---|
| | Polymer of Pre. Ex. 2 | Polymer of Pre. Ex. 3 | Polymer of Pre. Ex. 4 | Polymer of Pre. Ex. 5 |
| Amount of curing agent of Ex. 1 (g) | 0.04 | 0.11 | 0.16 | 0.13 |
| Amount of $H_2PtCl_6$ catalyst solution (μl) | 13 | 57 | 39 | 45 |
| Compatibility | Transparent Homogeneous | Slightly opaque Homogeneous | Slightly opaque Homogeneous | Slightly opaque Homogeneous |
| Snap-up time (80° C.) | 1'34" | 0'29" | 2'28" | 8'20" |

Note 1: The hydrosilyl group-containing curing agent of Example 1 and each of the polymers of Preparative Examples 2 to 5 were weighed so that the molar ratio of hydrosilyl group to allyl group was 1/1.
Note 2: The catalyst solution was added so that the amount of Pt was $1 \times 10^{-3}$ mol per one mol of the allyl group in each polymer.

Example 3

An Si—H group-containing ether curing agent (an amount indicated in Table 2) prepared in Example 1, each of various allyl group-containing polymers (9.54 g) prepared in Preparative Examples 2 to 5 and a chloroplatinic acid catalyst solution (an amount indicated in Table 2) used in Example 1 were intimately mixed with stirring. The mixture was defoamed by a centrifugal separation and cast in a mold made of polyethylene. The defoaming was again carried out at a room temperature under a reduced pressure, and the mixture was cured at 100° C. for one hour to obtain a

TABLE 2

| | Composition | | | |
|---|---|---|---|---|
| Experiment No. | 1 | 2 | 3 | 4 |
| Allyl group-containing organic polymer | Polymer of Pre. Ex. 2 | Polymer of Pre. Ex. 3 | Polymer of Pre. Ex. 4 | Polymer of Pre. Ex. 5 |
| Amount of curing agent of Example 1 (g) | 0.39 | 1.11 | 1.66 | 1.26 |
| Amount of $H_2PtCl_6$ catalyst solution (μl) | 11.4 | 3.6 | 5.2 | 4.5 |

TABLE 3

| | Tensile properties of cured material | | | | | | |
|---|---|---|---|---|---|---|---|
| Experiment No. | $M_{10}$ (kg/cm$^2$) | $M_{30}$ (kg/cm$^2$) | $M_{50}$ (kg/cm$^2$) | $M_{100}$ (kg/cm$^2$) | $M_{150}$ (kg/cm$^2$) | $T_B$ (kg/cm$^2$) | $E_B$ (%) |
| 1 | 0.3 | 0.9 | 1.3 | 2.0 | 2.3 | 2.7 | 164 |
| 2 | 2.8 | — | — | — | — | 5.6 | 23 |
| 3 | 2.0 | 5.1 | 7.4 | — | — | 7.1 | 47 |
| 4 | 1.2 | 3.3 | 5.6 | — | — | 7.5 | 64 |

Comparative Example 1

A cured material was prepared in the same manner as in Example 3 except that a polymethylhydro-dimethylsiloxane copolymer (average molecular weight: about 2,000 to 2,100, PS 123 manufactured by Chisso Kabushiki Kaisha) of the formula:

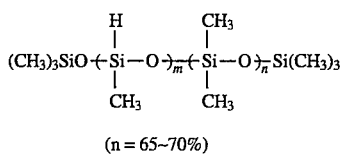

(n = 65~70%)

(an amount such that the molar ratio of the allyl group off each organic polymer to the hydrosilyl group of PS 123 was 1.) was used in stead of a hydrosilyl group-containing ether curing agent prepared in Example 1. Said polysiloxane had poor compatibility with each allyl group-containing organic polymer, and the mixture was opaque. Some of mixtures separated when they were kept standing for a long time. Many foams remained after the defoaming under a reduced pressure. Only a cured material containing many foams and having poor mechanical properties was obtained.

Example 4

Allyl ether-terminated polypropylene oxide (12.0 g) prepared in Preparative Example 2, a hydrosilyl group-containing ether curing agent (0.49 g) prepared in Example 1 (the molar ratio of the hydrosilyl group to the allyl group was 1.) and a chloroplatinic acid catalyst solution (14.3 μl) used in Example 1 were intimately mixed with stirring. The mixture was defoamed by a centrifugal separation and cast in a mold having a size of 6 cm (length)×0.8 cm (width)×1.8 cm (depth). The defoaming was again carried out at a room temperature under a reduced pressure, and the mixture was cured at 100° C. for 30 minutes to obtain a rubbery cured material having a thickness of 13 mm. A hardness was measured according to a hardness measuring method defined in a spring-method hardness test (A type) in JIS K 6301, paragraph 5-2. The cured material had a hardness of 22 on the obverse and a hardness of 21 also on the reverse. The sample having good depth curability was obtained.

Example 5

A 200 ml four-necked flask equipped with a stirring rod, a dropping funnel, a thermometer, a three-way cock and a condenser was used. In the flask, a cyclic hydrogenpolysiloxane:

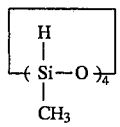

(LS 8600 manufactured by Shin-Etsu Chemical Co., Ltd.) (29.73 g, 124 mmol) was charged under a nitrogen atmosphere. After diallyl isophthalate ester (manufactured by Wako Junyaku Kabushiki Kaisha) (9.84 g, 40 mmol) and a solution of chloroplatinic acid catalyst (a solution in which $H_2PtC_6 \cdot 6H_2O$ (1.0 g) is dissolved in ethanol/1,2-dimethoxyethane (⅑ v/v) (9 g)) (82 μl) were dissolved in toluene (100 ml) and intimately mixed, the toluene solution was charged in the dropping funnel. The flask was heated to 65° to 70° C. and the toluene solution was dropwise added to the flask over 100 minutes. After the mixture was reacted for one hour, an IR spectra analysis was carried out. Since the complete disappearance of the olefin peak at 1640 cm$^{-1}$ was confirmed, the reaction was stopped. The reartion mixture was evaporated to remove volatile components and then dried at 80° C. under a reduced pressure for one hour to obtain a pale yellow viscous liquid (25.85 g). Analysis such as 300 MHz $^1$H NMR and IR spectra revealed that the viscous liquid is an ester curing agent having an Si—H group which has the following structure:

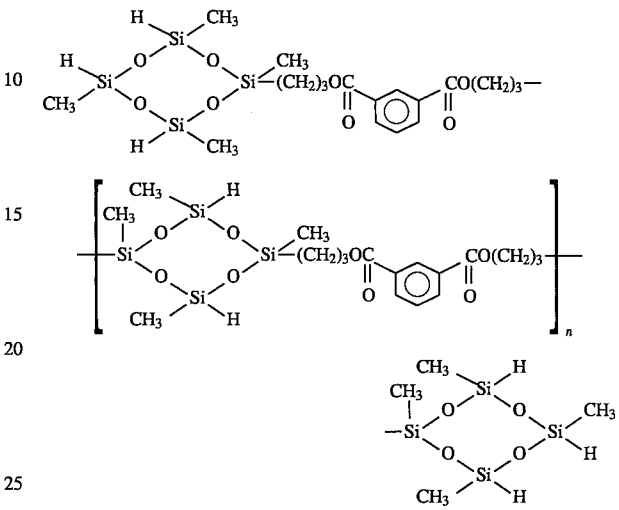

The measured proton intensity ratio (0.220) of Si—$\underline{H}$ to Si—C$\underline{H}_3$ according to 300 MHz $^1$H NMR spectra was compared with the calculated proton intensity.

When n is 1: 8/36=0.222

When n is 2: 10/48=0.208

The curing agent was a mixture consisting of, on the average, 86% of the compound (MW=1214) wherein n is 1 and 14% of the compound (MW=1701) wherein n is 2. On the basis of this, the number of Si-H groups per a unit weight was calculated to be 0.649 mol/100 g.

IR (neat, cm$^{-1}$): 3050 (w), 2940 (s), 2910 (s), 2150 (s, $v_{Si-H}$), 1720 (s, $v_{C=O}$), 1605 (m), 1300 (s), 1255 (s), 1070 (bs, $v_{SiOSi}$).

Figure 3:
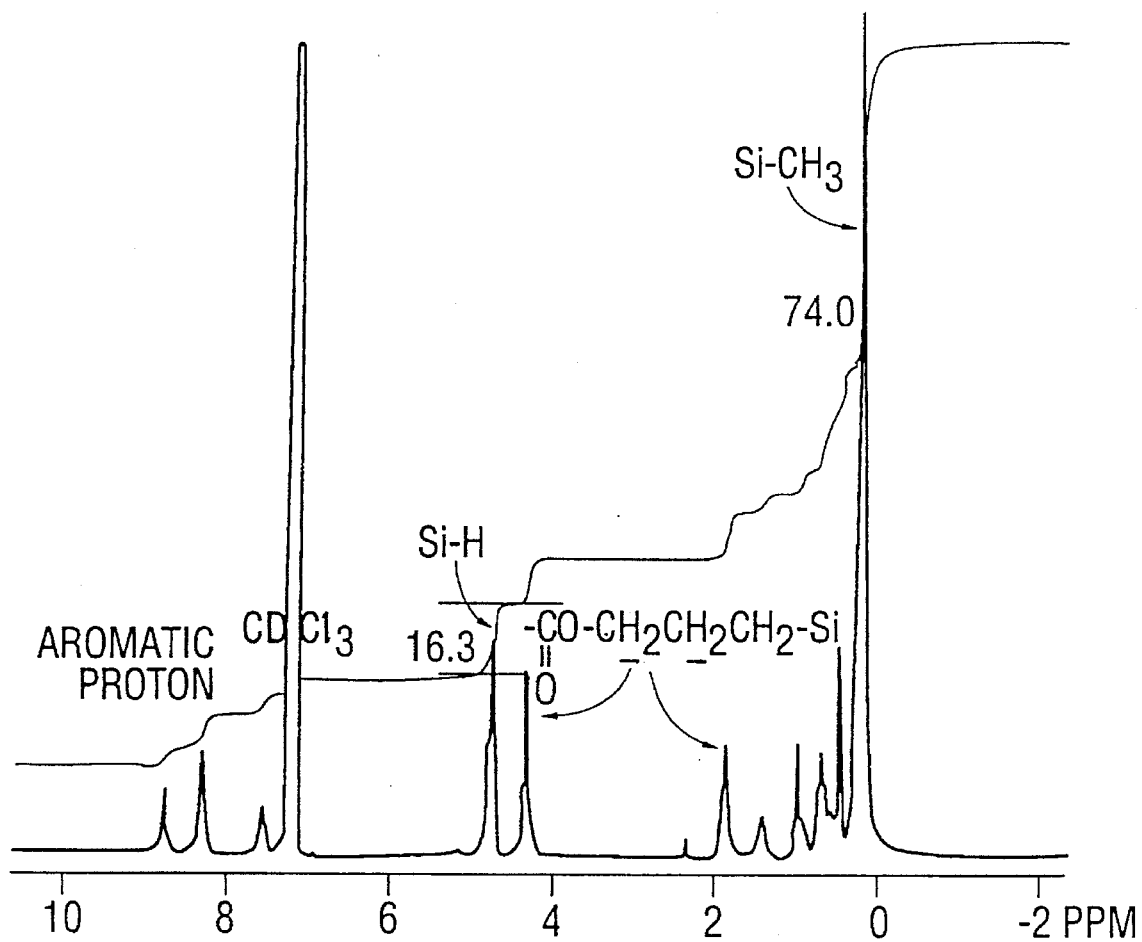
FIG. 3 is a 300 MHz $^1$H NMR spectrum chart of the Si—H group-containing ester curing agent obtained in Example 5.

$^1$H NMR (300 MHz): see FIG. 3.

Example 6

The compatibility of an Si—H group-containing ester curing agent prepared in Example 5 with allyl group-containing organic polymers having various backbones was examined. According to combinations indicated in Table 4, the curing agent (an indicated amount) and each of the organic polymers (1.30 g) prepared in Preparative Examples 2 to 6 were intimately mixed and centrifugally defoamed. Then, the mixed state was observed. Although some mixtures were slightly opaque, mixtures were generally transparent and homogeneous. Said Si-H group-containing ester curing agent had good compatibility with various organic polymers.

For examining the curability, a solution (an indicated amount) in which a chloroplatinic acid catalyst solution used in Example 5 was diluted to a tenth concentration was added to each of said mixtures and intimately mixed. A part of the mixture was transferred on a gelation testing device (manufactured by Nisshin Kagaku Kabushiki Kaisha) and a snap-up time (the time which is required for forming a rubbery elastomer) was measured at an indicated temperature. Results are shown in Table 4. The compositions had a rapid curability at a high temperature.

TABLE 4

Compatibility and curability of Si—H group-containing ester curing agent with allyl group-containing organic polymer

| | Allyl group-containing organic polymer | | | | |
|---|---|---|---|---|---|
| | Polymer of Pre. Ex. 2 | Polymer of Pre. Ex. 3 | Polymer of Pre. Ex. 4 | Polymer of Pre. Ex. 5 | Polymer of Pre. Ex. 6 |
| Amount of curing agent of Ex. 5 (g) | 0.05 | 0.21 | 0.14 | 0.16 | 0.11 |
| Amount of H$_2$PtCl$_6$ catalyst solution (μl) | 14.6 | 66.1 | 45.4 | 51.7 | 36.2 |
| Compatibility | Transparent Homogeneous | Transparent Homogeneous | Transparent Homogeneous | Slightly opaque Homogeneous | Transparent Homogeneous |
| Snap-up time (80° C.) | 1'26" | 5'24" | 0'29" | 5'23" | 1'05" |
| (100° C.) | 0'30" | 1'13" | 0'12" | 1'27" | 0'27" |
| (120° C.) | 0'23" | 0'28" | 0'11" | 0'30" | 0'25" |

Note 1: The hydrosilyl group-containing curing agent of Example 5 and each of the polymers of Preparative Examples 2 to 6 were weighed so that the molar ratio of hydrosilyl group to allyl group was 1/1.
Note 2: The catalyst solution was added so that the amount of Pt was $1 \times 10^{-3}$ mol per one mol of the allyl group in each polymer.

Example 7

An Si—H group-containing ester curing agent (an amount indicated in Table 5) prepared in Example 5, each of various allyl group-containing polymers (8.32 g) prepared in Preparative Examples 2 to 6 and a chloroplatinic acid catalyst solution (an amount indicated in Table 5) used in Example 5 were intimately mixed with stirring. The mixture was defoamed by a centrifugal separation and cast in a mold made of polyethylene. The defoaming was again carried out at a room temperature under a reduced pressure, and the mixture was cured at 80° C. for one hour to obtain a homogeneous rubbery cured material having a thickness of about 3 mm. A No. 3 dumbbell test piece according to JIS K 6301 was punched off from the sheet of the cured material, and a tensile test was carried out at a pulling speed of 200 mm/min. Results are shown in Table 5.

A homogeneous rubbery cured material can be prepared by a short time cure when the hydrosilyl group-containing ester curing agent is used according to the present invention.

Comparative Example 2

A cured material was prepared in the same manner as in Example 7 except that a polymethylhydro-dimethylsiloxane copolymer (average molecular weight: about 2,000 to 2,100, PS 123 manufactured by Chisso Kabushiki Kaisha) of the formula:

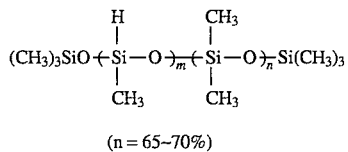

(n = 65~70%)

(an amount such that the molar ratio of the allyl group of each organic polymer to the hydrosilyl group of PS 123 was 1.) was used in stead of a hydrosilyl group-containing ester curing agent prepared in Example 5. Said polysiloxane had poor compatibility with each allyl group-containing organic polymer, and the mixture was opaque. Some of mixtures separated when they were kept standing for a long time. Many foams remained after the defoaming under a reduced pressure. Only a cured material containing many foams and having poor mechanical properties was obtained.

TABLE 5

Tensile properties of cured material

| Experiment No. | 5 | 6 | 7 | 8 | 9 |
|---|---|---|---|---|---|
| Allyl group-containing organic polymer | Polymer of Pre. Ex. 2 | Polymer of Pre. Ex. 3 | Polymer of Pre. Ex. 4 | Polymer of Pre. Ex. 5 | Polymer of Pre. Ex. 6 |
| Amount of curing agent of Ex. 5 (g) | 0.32 | 1.57 | 1.08 | 1.23 | 0.86 |
| Amount of H$_2$PtCl$_6$ catalyst solution (μl) | 5.5 | 5.0 | 3.4 | 4.0 | 5.0 |
| (Tensile properties) | | | | | |
| Strength (kg/cm$^2$) | 3.0 | 9.0 | 6.0 | 3.5 | 7.4 |
| Elongation (%) | 450 | 160 | 70 | 50 | 120 |

Example 8

Allyl ether-terminated polypropylene oxide (12.0 g) prepared in Preparative Example 2, a hydrosilyl group-containing ester curing agent (0.46 g) prepared in Example 5 (the molar ratio of the hydrosilyl group to the allyl group was 1.) and a chloroplatinic acid catalyst solution (8 μl) used in Example 5 were intimately mixed with stirring. The mixture was defoamed by a centrifugal separation and cast in a mold having a size of 6 cm (length)×0.8 cm (width)×1.8 cm (depth). The defoaming was again carried out at a room temperature under a reduced pressure, and the mixture was cured at 100° C. for 30 minutes to obtain a rubbery cured material having a thickness of 13 mm. A hardness was measured according to a hardness measuring method defined in a spring-method hardness test (A type) in JIS K 6301, paragraph 5-2. The cured material had a hardness of 20 on the obverse and a hardness of 19 on the reverse. The sample having good depth curability was obtained.

Example 9

A 200 ml four-necked flask equipped with a condenser having a three-way cock, a dropping funnel, a thermometer, a magnetic tip and a glass stopper was used. In the flask, a cyclic polyhydrogensiloxane:

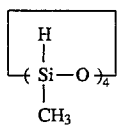

(LS 8600 manufactured by Shin-Etsu Chemical Co., Ltd.) (12.03 g, 50 mmol) and toluene (20 ml) were charged under a nitrogen atmosphere. After 1,9-decadiene (2.76 g, 20 mmol) and a solution of chloroplatinic acid catalyst (a solution in which $H_2PtCl_6 \cdot 6H_2O$ (1.0 g) is dissolved in ethanol (1 g) and 1,2-dimethoxyethane (9 g)) (20 μl) were dissolved in toluene (30 ml), the toluene solution was charged in the dropping funnel. The flask was immersed in an oil bath at 50° C. and the toluene solution was dropwise added to the flask over two hours under a nitrogen atmosphere. After the mixture was reacted at 50° C. for one hour, an IR spectra analysis was carried out. Since the complete disappearance of the olefin peak at 1640 cm$^{-1}$ was confirmed, the reaction was stopped. The toluene solution was washed with a saturated aqueous solution of ammonium chloride (100 ml×2) and deionized water (100 ml×1) and dried with $Na_2SO_4$. $Na_2SO_4$ was removed by filtering. The mixture was evaporated to remove volatile components and then dried at 80° C. under a reduced pressure to obtain a colorless transparent liquid (9.11 g). A hydrosilyl group in the hydrocarbon curing agent was confirmed as a strong peak at 2170 cm$^{-1}$. By comparing the measured proton intensity ratio (0,216) of Si—$\underline{H}$ to Si—$\underline{CH}_3$ according to 300 MHz $^1$H NMR spectra with the calculated proton intensity, the curing agent was revealed to be a mixture having the following structure (on the average, 53% of the compound (MW =998) wherein n is 1 and 47% of the compound (MW =1377) wherein n is 2). On the basis of this, the number of Si—H groups per a unit weight was calculated to be 0.769 mol/100 g.

bones was examined. According to combinations indicated in Table 6, the curing agent (indicated amount) and the organic polymer (1.0 g) were intimately mixed and centrifugally defoamed. Then, the mixed state was observed. Although some mixtures were slightly opaque, mixtures were generally transparent and homogeneous. Said Si—H group-containing hydrocarbon curing agent had good compatibility with various organic polymers.

For examining the curability, a solution (indicated amount) in which the chloroplatinic acid catalyst solution used in Example 9 was diluted to a tenth concentration was added to each of said mixtures and intimately mixed. A part of the mixture was transferred on a gelation testing device (manufactured by Nisshin Kagaku Kabushiki Kaisha) and a snap-up time (the time which is required for forming a rubbery elastomer) was measured at 100° C. Results are shown in Table 6. The compositions had a rapid curability at a high temperature.

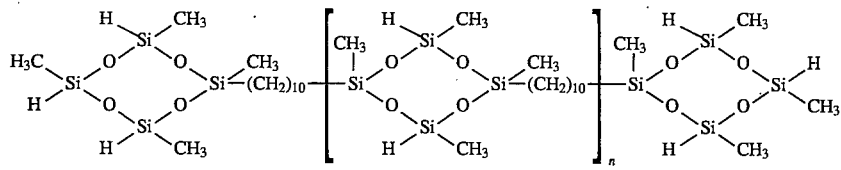

Example 10

The compatibility of an Si—H group-containing hydrocarbon curing agent prepared in Example 9 with allyl group-containing organic polymers having various back-

TABLE 6

Compatibility and curability of Si—H group-containing hydrocarbon curing agent with allyl group-containing organic polymer

|  | Allyl group-containing organic polymer | | | |
|---|---|---|---|---|
|  | Polymer of Pre. Ex. 2 | Polymer of Pre. Ex. 3 | Polymer of Pre. Ex. 4 | Polymer of Pre. Ex. 5 |
| Amount of curing agent of Ex. 9 (g) | 0.03 | 0.09 | 0.14 | 0.10 |
| Amount of $H_2PtCl_6$ catalyst solution (μl) | 9 | 29 | 40 | 33 |
| Compatibility | Transparent Homogeneous | Slightly opaque Homogeneous | Slightly opaque Homogeneous | Slightly opaque Homogeneous |
| Snap-up time (100° C.) | 0'37" | 0'12" | 0'31" | 3'00" |

Note 1: The hydrosilyl group-containing curing agent of Example 9 and each of the polymers of Preparative Examples 2 to 5 were weighed so that the molar ratio of hydrosilyl group to allyl group was 1/1.
Note 2: The catalyst solution was added so that the amount of Pt was $1 \times 10^{-3}$ mol per one mol of the allyl group in each polymer.

Example 11

An Si—H group-containing hydrocarbon curing agent (an amount indicated in Table 7) prepared in Example 9, each of various allyl group-containing polymers (an indicated amount) prepared in Preparative Examples 2 and 4 and a chloroplatinic acid catalyst solution used in Example 9 (an indicated amount) were intimately mixed with stirring. The mixture was defoamed by a centrifugal separation and cast in a mold made of polyethylene. The defoaming was again carried out at a room temperature under a reduced pressure, and the mixture was cured at 100° C. for one hour to obtain a homogeneous rubbery cured material having a thickness of about 3 mm. A No. 3 dumbbell test piece according to JIS K 6301 was punched off from the sheet of the cured material, and a tensile test was carried out at a pulling speed of 200 mm/min. Results are shown in Table 7.

Table 7 shows that a homogeneous rubbery cured material can be prepared by a short time cure when the hydrosilyl group-containing hydrocarbon curing agent is contained in the composition according to the present invention.

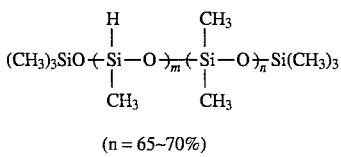

(n = 65~70%)

(an amount such that the molar ratio of the allyl group of each organic polymer to the hydorosilyl group of PS 123 was 1.) was used in stead of a hydrosilyl group-containing hydrocarbon curing agent prepared in Example 9. Said polysiloxane had poor compatibility with each allyl group-containing organic polymer, and the mixture was opaque. Some of mixtures separated when they were kept standing for a long time. Many foams remained after the defoaming under a reduced pressure. Only a cured material containing many foams and having poor mechanical properties was obtained.

TABLE 7

| Experiment No. | Allyl group-containing organic polymer Type | Amount (g) | Amount of Si—H group-containing curing agent of Example 9 (g) | Amount of $H_2PtCl_6$ catalyst solution (μl) | Tensile properties $E_B$ (%) | $T_B$ (kg/cm²) |
|---|---|---|---|---|---|---|
| 10 | Polymer of Pre. Ex. 2 | 10.73 | 0.33 | 1.0 | 246 | 2.9 |
| 11 | Polymer of Pre. Ex. 4 | 8.94 | 1.22 | 3.8 | 44 | 8.1 |

Comparative Example 3

A cured material was prepared in the same manner as in Example 11 except that a polymethylhydro-dimethylsiloxane copolymer (average molecular weight: about 2,000 to 2,100, PS 123 manufactured by Chisso Kabushiki Kaisha) of the formula:

Example 12

Allyl ether-terminated polypropylene oxide (10.0 g) prepared in Preparative Example 2, a hydrosilyl group-containing hydrocarbon curing agent (0.30 g) prepared in Example 9 (the molar ratio of the hydrosilyl group to the allyl group was 1.) and a chloroplatinic acid catalyst solution (10 μl) used in Example 9 were intimately mixed with stirring. The mixture was cast in a polyethylene test tube having a size of about 1.5 cm (diameter)×about 10 cm (length) and defoamed by centrifugal separation and at a room temperature under a reduced pressure. Then, the mixture was cured at 80° C. for one hour. After curing, a bottom part of the tube was cut and a cut surface was observed. The mixture was cured homogeneously.

Example 13

A 200 ml four-necked flask equipped with a condenser having a three-way cock, a dropping funnel, a thermometer, a magnetic tip and a glass stopper was used. In the flask, a cyclic polyhydrogensiloxane:

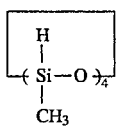

(LS 8600 manufactured by Shin-Etsu Chemical Co., Ltd. ) (12.03 g, 50 mmol) and toluene (20 ml) were charged under a nitrogen atmosphere. After diethylene glycol diallyl carbonate:

(RAV-7N, manufactured by Mitsui Petrochemical Industries, Ltd.) (5.49 g, 20 mmol) and a solution of chloroplatinic acid catalyst (a solution in which $H_2PtCl_6 \cdot 6H_2O$ (1.0 g) is dissolved in ethanol (1 g) and 1,2-dimethoxyethane (9 g)) (41 μl) were dissolved in toluene (50 ml), the toluene solution was charged in the dropping funnel. The flask was immersed in an oil bath at 50° C. and the toluene solution was dropwise added to the flask over 1.5 hours under a nitrogen atmosphere. After the addition, an IR spectra analysis was carried out. Since the complete disappearance of the olefin peak at 1640 cm$^{-1}$ was confirmed, the reaction was stopped. The reaction mixture was evaporated to remove volatile components and to obtain a pale yellow transparent slightly viscous liquid (10.2 g). The hydrosilyl group of the carbonate compound was confirmed as a strong peak at 2170 cm$^{-1}$ according to IR spectra. By comparing the measured proton intensity ratio (0.181) of Si—$\underline{H}$ to Si—$\underline{CH_3}$ according to 300 MHz $^1$H NMR spectra with the calculated proton intensity, the curing agent was revealed to be one having the following structure on the average. On the basis of this, the number of Si—H groups per a unit weight was calculated to be 0.47 mol/100 g.

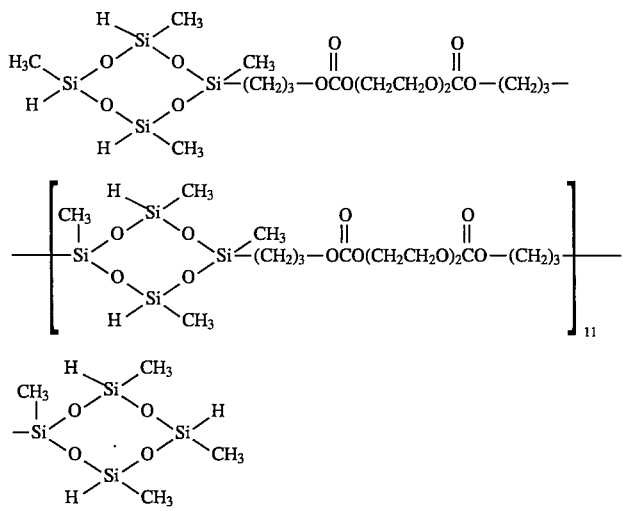

Example 14

The compatibility of an Si—H group-containing carbonate compound prepared in Example 13 with allyl group-containing organic polymers having various backbones was examined. According to combinations indicated in Table 8, the carbonate compound (an indicated amount) and the organic polymer (1.0 g) were intimately mixed and centrifugally defoamed. Then, the mixed state was observed. Although some mixtures were slightly opaque, mixtures were generally transparent and homogeneous. Said Si—H group-containing carbonate compound had good compatibility with various organic polymers.

For examining the curability, a solution (an indicated amount) in which a chloroplatinic acid catalyst solution used in Example 13 was diluted to a tenth concentration was added to each of said mixtures and intimately mixed. A part of the mixture was transferred on a gelation testing device (manufactured by Nisshin Kagaku Kabushiki Kaisha) and a snap-up time (the time which is required for forming a rubbery elastomer) was measured at 80° C. Results are shown in Table 8. The compositions had a rapid curability at a high temperature.

TABLE 8

Compatibility and curability of Si—H group-containing carbonate compound with allyl group-containing organic polymer

| | Allyl group-containing organic polymer | | | | |
|---|---|---|---|---|---|
| | Polymer of Pre. Ex. 2 | Polymer of Pre. Ex. 3 | Polymer of Pre. Ex. 4 | Polymer of Pre. Ex. 5 | Polymer of Pre. Ex. 6 |
| Amount of compound of Ex. 13 (g) | 0.05 | 0.16 | 0.22 | 0.18 | 0.12 |
| Amount of $H_2PtCl_6$ catalyst solution (μl) | 12 | 37 | 54 | 43 | 29 |
| Compatibility | Transparent Homogeneous | Slightly opaque Homogeneous | Slightly opaque Homogeneous | Slightly opaque Homogeneous | Slightly opaque Homogeneous |
| Snap-up time (80° C.) | 1'11" | 0'25" | 4'30" | 8'45" | 1'19" |

Note 1: The hydrosilyl group-containing compound of Example 13 and each of the polymers of Preparative Examples 2 to 6 were weighed so that the molar ratio of hydrosilyl group to allyl group was 1/1.
Note 2: The catalyst solution was added so that the amount of Pt was $1 \times 10^{-3}$ mol per one mol of the allyl group in each polymer.

Example 15

An Si—H group-containing carbonate compound (an indicated amount in Table 9) prepared in Example 13, each of various allyl group-containing polymers (10 g) prepared in Preparative Examples 2 to 4 and a chloroplatinic acid catalyst solution used in Example 13 (an indicated amount in Table 9) were intimately mixed with stirring. The mixture was defoamed by a centrifugal separation and cast in a mold made of polyethylene. The defoaming was again carried out at a room temperature under a reduced pressure, and the mixture was cured at 80° C. for one hour to obtain a homogeneous rubbery cured material having a thickness of about 3 mm. A No. 3 dumbbell test piece according to JIS K 6301 was punched off from the sheet of the cured material, and a tensile test was carried out at a pulling speed of 200 mm/min. Results are shown in Table 10.

Table 10 shows that a homogeneous rubbery cured material can be prepared by a short time cure when the hydrosilyl group-containing carbonate compound is used according to the present invention.

TABLE 9

| | Composition | | |
|---|---|---|---|
| Experiment No. | 12 | 13 | 14 |
| Allyl group-containing organic polymer | Polymer of Pre. Ex. 2 | Polymer of Pre. Ex. 3 | Polymer of Pre. Ex. 4 |
| Amount of compound of Example 13 (g) | 0.5 | 1.6 | 2.2 |
| Amount of $H_2PtCl_6$ catalyst solution (μl) | 12 | 37 | 54 |

TABLE 10

| | Tensile properties of cured material | | | | | | |
|---|---|---|---|---|---|---|---|
| Experiment No. | $M_{10}$ (kg/cm²) | $M_{30}$ (kg/cm²) | $M_{50}$ (kg/cm²) | $M_{100}$ (kg/cm²) | $M_{150}$ (kg/cm²) | $T_B$ (kg/cm²) | $E_B$ (%) |
| 12 | 0.4 | 1.0 | 1.4 | 2.2 | 2.9 | 6.8 | 402 |
| 13 | 2.8 | 6.6 | — | — | — | 8.2 | 42 |
| 14 | 1.9 | 4.7 | 7.4 | — | — | 6.0 | 43 |

Comparative Example 4

A cured material was prepared in the same manner as in Example 15 except that a polymethylhydro-dimethylsiloxane copolymer (average molecular weight: about 2,000 to 2,100, PS 123 manufactured by Chisso Kabushiki Kaisha) of the formula:

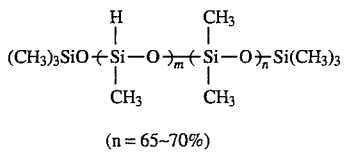

(n = 65~70%)

(an amount such that the molar ratio of the allyl group of each organic polymer to the hydrosilyl group of PS 123 was 1.) was used in stead of a hydrosilyl group-containing carbonate compound prepared in Example 13. Said polysiloxane had poor compatibility with each allyl group-containing organic polymer, and the mixture was opaque. Some of mixtures separated when they were kept standing for a long time. Many foams remained after the defoaming under a reduced pressure. Only a cured material containing many foams and having poor mechanical properties was obtained.

Example 16

Allyl ether-terminated polypropylene oxide (10.0 g) prepared in Preparative Example 2, a hydrosilyl group-containing carbonate compound (0.5 g) prepared in Example 13 (the molar ratio of the hydrosilyl group to the allyl group was 1.) and a chloroplatinic acid catalyst solution (12 μl) used in Example 13 were intimately mixed with stirring. The mixture was cast in a polyethylene test tube having a size of about 1.5 cm (diameter)×about 10 cm (length) and defoamed

What is claimed is:

1. An organic curing agent having at least two hydrosilyl groups in a molecule, which is prepared by reacting (A) a non-polymeric organic compound having at least one alkenyl group in a molecule, of the formula:

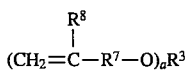

wherein $R^7$ is a hydrocarbon group having 0 to 18 carbon atoms which may have at least one ether linkage, $R^8$ is a hydrogen atom or a methyl group, $R^3$ is an organic group having 1 to 30 carbon atoms, and a is an integer of 1 to 4, the formula:

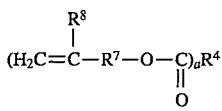

wherein $R^7$ is a hydrocarbon group having 0 to 18 carbon atoms which may have at least one ether linkage, $R^8$ is a hydrogen atom or a methyl group, $R^4$ is an organic group having 1 to 30 carbon atoms, and a is an integer of 1 to 4, the formula:

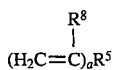

wherein $R^8$ is a hydrogen atom or a methyl group, $R^5$ is a mono-, di-, tri-, or tetra-valent hydrocarbon group having 2 to 50 carbon atoms, and a is an integer of 1 to 4, or the formula:

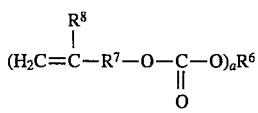

wherein $R^7$ is a hydrocarbon group having 0 to 18 carbon atoms which may have at least one ether linkage, $R^8$ is a hydrogen atom and a methyl group, $R^6$ is an organic group having 1 to 30 carbon atoms, and a is an integer of 1 to 4, with (B) a polyvalent hydrogensilicon compound of the formula:

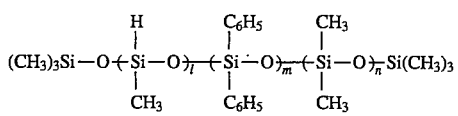

wherein $1 \geq 2$ and $1+m+n=3-50$, or the formula:

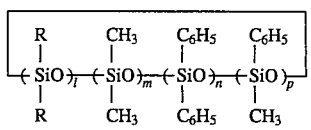

wherein $1 \geq 2$, $p+1+m+n=3-20$, and $R=CH_3$, $C_2H_5$, or $C_6H_5$, in the presence of a hydrosilylation catalyst so that at least two hydrosilyl groups remain after the reaction.

2. The organic curing agent according to claim 1, which is a compound having at least one group selected from the group consisting of the formulas:

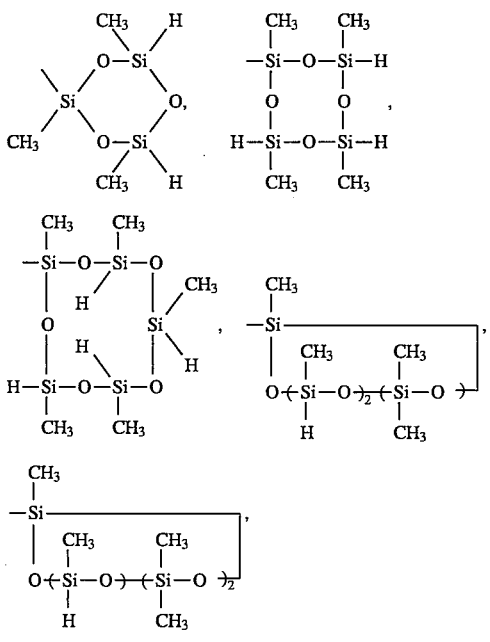

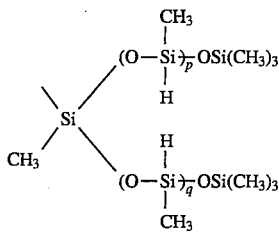

and

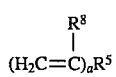

wherein p is a positive integer and q is 0 or a positive integer provided that $2 \leq p+q \leq 4$.

3. A method for preparing an organic curing agent having at least two hydrosilyl groups in a molecule, which method comprises reacting (A) a non-polymeric organic compound having at least one alkenyl group in a molecule, of the formula:

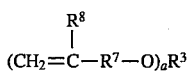

wherein $R^7$ is a hydrocarbon group having 0 to 18 carbon atoms which may have at least one ether linkage, $R^8$ is a hydrogen atom or a methyl group, $R^3$ is an organic group having 1 to 30 carbon atoms, and a is an integer of 1 to 4, the formula:

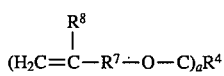

wherein $R^7$ is a hydrocarbon group having 0 to 18 carbon atoms which may have at least one ether linkage, $R^8$ is a hydrogen atom or a methyl group, $R^4$ is an organic group having 1 to 30 carbon atoms, and a is an integer of 1 to 4, the formula:

$(H_2C=C)_aR^5$ wherein $R^8$ is a hydrogen atom or a methyl group, $R^5$ is a mono-, di-, tri-, or tetra-valent hydrocarbon group having 2 to 50 carbon atoms, and a is an integer of 1 to 4, or the formula:

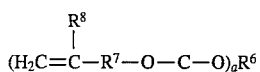

wherein $R^7$ is a hydrocarbon group having 0 to 18 carbon atoms which may have at least one ether linkage, $R^8$ is a hydrogen atom and a methyl group, $R^6$ is an organic group having 1 to 30 carbon atoms, and a is an integer of 1 to 4, with (B) a polvalent hydrogensilicon compound of the formula:

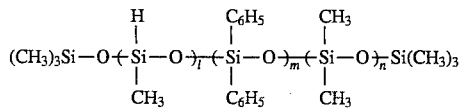

wherein $l \geq 2$ and $1+m+n=3-50$, or the formula:

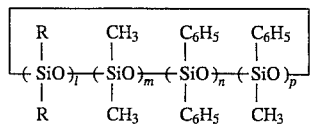

wherein $l \geq 2$, $p+l+m+n=3-20$, and $R=CH_3$, $C_2H_5$, or $C_6H_5$, in the presence of a hydrosilylation catalyst so that at least two hydrosilyl groups remain after the reaction.

4. The method according to claim 3, wherein the polyvalent hydrogensilicon compound (B) is a polyvalent hydrogenpolysiloxane having at least three hydrosilyl groups in one molecule and a molecular weight of less than 500.

5. The method according to claim 4, wherein the polyvalent hydrogensilicon compound (B) is one selected from the group consisting of compounds of the formulas:

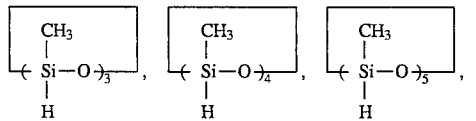

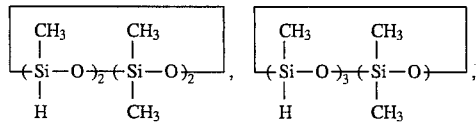

and

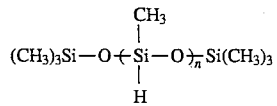

wherein $n=3-5$.

* * * * *